United States Patent
Fu et al.

(10) Patent No.: US 7,368,257 B2
(45) Date of Patent: May 6, 2008

(54) MODULATORS OF LYMPHOCYTE ACTIVATION, MKK3B COMPOSITIONS AND METHODS OF USE

(75) Inventors: Alan C. Fu, Union City, CA (US); Jun Wu, Shanghai (CN); X. Charlene Liao, Palo Alto, CA (US); Helena Mancebo, Fremont, CA (US)

(73) Assignee: Rigel Pharmaceuticals, Incorporated, South San Francisco, CA (US)

( * ) Notice: Subject to any disclaimer, the term of this patent is extended or adjusted under 35 U.S.C. 154(b) by 76 days.

(21) Appl. No.: 10/495,901

(22) PCT Filed: Nov. 18, 2002

(86) PCT No.: PCT/US02/36881

§ 371 (c)(1),
(2), (4) Date: Dec. 28, 2004

(87) PCT Pub. No.: WO03/044529

PCT Pub. Date: May 30, 2003

(65) Prior Publication Data

US 2005/0170434 A1 Aug. 4, 2005

Related U.S. Application Data

(60) Provisional application No. 60/332,441, filed on Nov. 16, 2001.

(51) Int. Cl.
*C12Q 1/48* (2006.01)
*C12Q 1/02* (2006.01)
*C12P 21/06* (2006.01)

(52) U.S. Cl. .......................... 435/15; 435/29; 435/69.1

(58) Field of Classification Search .................... None
See application file for complete search history.

(56) References Cited

OTHER PUBLICATIONS

Macian F., NFAT proteins: key regulators of T-cell development and function. Nat Rev Immunol. Jun. 2005;5(6):472-84. Review.*
Chen et al, Role of NFATx (NFAT4/NFATc3) in expression of immunoregulatory genes in murine peripheral CD4+ T cells. J Immunol. Mar. 15, 2003;170(6):3109-17.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Han et al, Identification and characterization of a predominant isoform of human MKK3. FEBS Lett. Feb. 10, 1997;403(1):19-22.*
Lu et al, Defective IL-12 production in mitogen-activated protein (MAP) kinase kinase 3 (Mkk3)-deficient mice. EMBO J. Apr. 1, 1999;18(7):1845-57.*
Moriguchi et al, Purification and identification of a major activator for p38 from osmotically shocked cells. Activation of mitogen-activated protein kinase kinase 6 by osmotic shock, tumor necrosis factor-alpha, and H2O2. J Biol Chem. Oct. 25, 1996;271(43):26981-8.*

* cited by examiner

*Primary Examiner*—Sheridan Swope
(74) *Attorney, Agent, or Firm*—Klarquist Sparkman LLP

(57) ABSTRACT

The present invention provides compositions and methods for modulating lymphocyte activation. Nucleic acids encoding proteins and proteins so encoded which are capable of modulating lymphocyte activation are provided. Compositions and methods for the treatment of disorders related to lymphocyte dysfunction or dysregulation are also provided. Prophylactics and methods for the prevention of such disorders are also provided. Also provided are compositions and methods for diagnostic and prognostic determination of such disorders. Further provided are assays for the identification of bioactive agents capable of modulating lymphocyte activation.

10 Claims, 13 Drawing Sheets

FIGURE 5

```
   1   ctcgagatcc attgtgctct aaagagtctc caccgccgtc caggacccac ttgcagcatg
  61   gagtcgcccg cctcgagcca gcccgccagc atgccccagt ccaaaggaaa atccaagagg
 121   aagaaggatc tacggatatc ctgcatgtcc aagccacccg cacccaaccc cacaccccccc
 181   cggaacctgg actcccggac cttcatcacc attggagaca gaaactttga ggtggaggct
 241   gatgacttgg tgaccatctc agaactgggc cgtggagcct atggggtggt agagaaggtg
 301   cggcacgccc agagcggcac catcatggcc gtgaagcgga tccgggccac cgtgaactca
 361   caggagcaga gcggctgct catggacctg gacatcaaca tgcgcacggt cgactgtttc
 421   tacactgtca ccttctacgg ggcactattc agagagggag acgtgtggat ctgcatggag
 481   ctcatggaca catccttgga caagttctac cggaaggtgc tggataaaaa catgacaatt
 541   ccagaggaca tccttgggga gattgctgtg tctatcgtgc gggccctgga gcatctgcac
 601   agcaagctgt cggtgatcca cagagatgtg aagccctcca atgtccttat caacaaggag
 661   ggccatgtga agatgtgtga ctttggcatc agtggctact ggtggactc tgtggccaag
 721   acgatggatg ccggctgcaa gccctacatg gcccctgaga ggatcaaccc agagctgaac
 781   cagaagggct acaatgtcaa gtccgacgtc tggagcctgg gcatcaccat gattgagatg
 841   gccatcctgc ggttcccta cgagtcctgg gggacccgt tccagcagct gaagcaggtg
 901   gtggaggagc cgtccccca gctcccagcc gaccgtttct cccccgagtt tgtggacttc
 961   actgctcagt gcctgaggaa gaaccccgca gagcgtatga gctacctgga gctgatggag
1021   cacccctct tcaccttgca caaaaccaag aagacggaca ttgctgcctt cgtgaaggag
1081   atcctgggag aagactcata ggggctgggc ctcggacccc actccggccc tccagagccc
1141   cacagcccca tctgcggggg cagtgctcac ccacaccata agctactgcc atcctggccc
1201   agggcatctg ggaggaaccg aggggctgc tcccacctgg ctctgtggcg agccatttgt
1261   cccaagtgcc aaagaagcag accattgggg ctcccagcca ggcccttgtc ggccccacca
1321   gtgcctctcc ctgctgctcc taggacccgt ctccagctgc tgagatcctg gactgagggg
1381   gcctggatgc ccctgtgga tgctgctgcc ctgcacagc aggctgccag tgcctgggtg
1441   gatgggccac cgccttgccc agcctggatg ccatccaagt tgtatatttt tttaatctct
1501   cgactgaatg gactttgcac actttggccc agggtggcca cacctctatc ccggctttgg
1561   tgcggggtac acaagagggg atgagttgtg tgaatacccc aagactccca tgagggagat
1621   gccatgagcc gcccaaggcc ttccctggc actggcaaac agggcctctg cggagcacac
1681   tggctcaccc agtcctgccc gccaccgtta tcggtgtcat tcacctttcg tgtttttttt
1741   aatttatcct ctgttgattt tttctttgc tttatgggtt tggcttgttt ttcttgcatg
1801   gtttggagct gatcgcttct cccccacccc ctagggtacc agcaggcaga gccttgccct
1861   ctgctcaggc tggggtccag tgggagggc ccaaaatctc tgctcagaga agtgcagggg
1921   gagccttcca gctcactctc cctgaggact ggcgtgacag gggctatggg tgttgttttt
1981   aaaaaagaa atatatttt tttgaaaaaa cgactgccca tcccgggtcc tttccctgat
2041   gggttggggc agttacctgg ttgctgtttt aattaaaaac tttagagcac aatggatctc
2101   gag human Mkk3b
cds : 58-1101
```

FIGURE 6

```
1    mespassqpa smpqskgksk rkkdlriscm skppapnptp prnldsrtfi tigdrnfeve
61   addlvtisel grgaygvvek vrhaqsgtim avkriratvn sqeqkrllmd ldinmrtvdc
121  fytvtfygal fregdvwicm elmdtsldkf yrkvldknmt ipedilgeia vsivralehl
181  hsklsvihrd vkpsnvlink eghvkmcdfg isgylvdsva ktmdagckpy maperinpel
241  nqkgynvksd vwslgitmie mailrfpyes wgtpfqqlkq vveepspqlp adrfspefvd
301  ftaqclrknp aermsylelm ehpfftlhkt kktdiaafvk eilgeds
``` human Mkk3b

Overexpression of Mkk3b Synergized with Calcium Signal to Activate NFAT in Jurkat Cells Constructs Used for Functional Studies Both CD40L and α-IgM Activate MKK3/MKK6 in Purified Primary B Cells

FIGURE 11

Optimization of B Cell Stimulation

CD19+ Splenocyte Stimulation Conditions*

| | CD40L (1:4) | α-CD40 10 μg/mL | α-IgM 10 μg/mL | LPS 20 μg/mL | PMA 50 ng/mL |
|---|---|---|---|---|---|
| CD80 | 1.5 | 3.8 | 2.7 | 2.5 | 1.0 |
| CD86 | 3.2 | 8.8 | 28.0 | 9.5 | 1.0 |
| CD69 | 4.8 | 7.5 | 8.3 | 7.8 | 2.2 |
| CD25 | 1.8 | 1.9 | 3.2 | 2.3 | 1.5 |
| CD54 | 3.3 | 4.8 | 5.2 | 4.7 | 1.0 |

*Plotted as fold induction over unstimulated cells

MKK3 Deficient Cells Exhibit Defects in CD80 Upregulation

MKK3 Deficient Cells Exhibit Defects in CD25 and CD69 Upregulation

MODULATORS OF LYMPHOCYTE ACTIVATION, MKK3B COMPOSITIONS AND METHODS OF USE

FIELD OF THE INVENTION

The present invention relates to signal transduction mechanisms involved in the modulation of lymphocyte activation. Compositions and methods for modulating lymphocyte activation are provided, as are methods for diagnosing and treating diseases associated with lymphocyte activation.

BACKGROUND OF THE INVENTION

The immune response comprises a cellular response and a humoral response. The cellular response is mediated largely by T-lymphocytes (alternatively and equivalently referred to herein as T cells), while the humoral response is mediated by B-lymphocytes (alternatively and equivalently referred to herein as B-cells).

B-cells produce and secrete antibodies in response to the presentation of antigen and MHC class II molecules on the surface of antigen presenting cells. Antigen presentation initiates B-cell activation with the engagement of the B-cell receptor (BCR) at the cell's surface. Following engagement, the BCR relays signals that are propagated through the cell's interior via signal transduction pathways. These signals lead to changes in B-cell gene expression and physiology, which underlie B-cell activation.

T cells produce costimulatory molecules, including soluble cytokines and cell surface proteins, that augment antibody production by B-cells during the humoral immune response. Cytokines also play a role in modulating the activity of T cells themselves. Many T cells act directly to engulf and destroy cells or agents that they recognize by virtue of the cell surface proteins they possess. The engagement of cell surface receptors on T cells results in the propagation of intracellular signals that provoke changes in T cell gene expression and physiology, which underlie the cellular immune response. B-cells in turn express cell surface proteins that modulate the activity of T cells and cellular immunity.

Antigen recognition alone is usually not sufficient to initiate a complete effector T or B cell response. The generation of many B-cell responses to antigen is dependent upon the interaction of B-cells with CD4+ helper T cells directed against the same antigen. These helper T cells express the CD40 ligand "CD40L" (also known as CD154) which binds to the cell surface receptor, CD40, on resting B-cells. This interaction provides a critical activation signal to B-cells. Mutations in the CD40L lead to the X-linked immunodeficiency disorder hyper-IgM syndrome, which is characterized by low levels of IgA and IgG, normal to elevated levels of IgM, absence of germinal center formation, and decreased immune response. In addition, transgenic mice lacking CD40 exhibit reduced graft rejection. (Zanelli et al., Nature Medicine, 6: 629-630, 2000; Schonbeck et al., Cell Mol Life Sci, 58:4-43, 2001).

CD40L expression on helper T cells is in turn regulated by the expression of CD80 on B cells. CD80 interacts with the T cell surface receptors CD28 and CD154 to modulate the activity of T cells, including the B cell-modulating activity of T cells (Sperling et al., 153:155-182, 1996). CD80 expression is in turn regulated by CD40 activity in B cells.

CD80 is expressed in a variety of antigen presenting cells (APCs) including B cells and dendritic cells and is essential for T cell co-stimulation. When T cells encounter peptide-MHC complexes on an APC, CD28 acts in conjunction with the TCR to produce a maximal cellular response. CD80 is currently being evaluated as a target for the treatment of clinical conditions including transplantation, graft-versus-host disease, psoriasis, and rheumatoid arthritis.

Non-lymphocyte myeloid derivatives are also activated by surface receptor engagement in immune response and in response to injury. For example, mast cells and basophils are activated by binding of antigen to surface IgE, while platelets are activated by the binding of thrombin to its receptor.

Intercellular communication between different types of lymphocytes, as well as between lymphocytes and non-lymphocytes in the normally functioning immune system is well known. Much of this communication is mediated by cytokines and their cognate receptors. Cytokine-induced signals begin at the cell surface with a cytokine receptor and are transmitted intracellularly via signal transduction pathways. Many types of cells produce cytokines, and cytokines can induce a variety of responses in a variety of cell types, including lymphocytes. The response to a cytokine can be context-dependent as well as cell type-specific.

In addition, the expression of cytokine receptor subunits may be dynamically regulated. For example, the II-2 receptor $\alpha$-subunit (CD25) is dynamically regulated in B cells and expression has been associated with leukemia (de Totero et al., Leukemia 9:1425-1431, 1995; Leonard et al., Cold Spring Harbor Symp. Quant. Biol., 64:417-424, 1999).

Dysregulation of intercellular communication can perturb lymphocyte activation and the regulation of immune responses. Such dysregulation is believed to underlie certain autoimmune disease states, hyper-immune states, and immune-compromised states. Such dysfunction may be cell autonomous or non-cell autonomous with respect to lymphocytes.

The activation of specific signaling pathways in lymphocytes determines the quality, magnitude, and duration of immune responses. In response to transplantation, in acute and chronic inflammatory diseases, and in autoimmune responses, it is these pathways that are responsible for the induction, maintenance and exacerbation of undesirable lymphocyte responses. Identification of these signaling pathways is desirable in order to provide diagnostic and prognostic tools, as well as therapeutic targets for modulating lymphocyte function in a variety of disorders or abnormal physiological states. In addition, the ability to modulate these pathways and suppress normal immune responses is often desirable, for example in the treatment of hosts receiving a transplant.

While the extracellular domains and cognate ligands of lymphocyte receptors vary widely, many receptors have similar intracellular domains (such as the "immunoreceptor tyrosine-based activation motif" (ITAM)), and associate with common intracellular signaling molecules.

Tyrosine kinase activation is a critical event in the propagation of intracellular signals by many receptors on lymphocytes, including antigen receptors on B and T cells (for a review see Turner et al, Immunology Today, 21:148-154, 2000, incorporated herein in its entirety by reference).

With regard to the B-cell antigen receptor (BCR), the BCR is rapidly phosphorylated on tyrosine residues following engagement of the receptor by antigen or other crosslinking agents. This tyrosine phosphorylation leads to associations with several SH2-containing signaling proteins. SH2-containing proteins are known to bind to phosphorylated tyrosine residues in the context of specific amino acid sequences (Pawson, Nature, 373:573-580, 1995; Pawson et al., Science, 278:2075-2080, 1997).

Many non-receptor tyrosine kinases have been shown to interact with tyrosine phosphorylated receptors in lymphocytes, including the antigen receptors of B and T cells. These non-receptor tyrosine kinases include members of the src family and the Bruton's tyrosine kinase (BTK) family. Importantly, many of these genes are associated with oncogenesis (van Leeuwen et al., Curr. Opin. Immunol., 11:242-248, 1999).

Btk is a non-receptor tyrosine kinase that is involved in the BCR signaling pathway and is critical for B cell development (for a review, see Tsukada et al., Advances in Immunology, 77:123-162, 2001; incorporated herein by reference). Btk was originally identified as a tyrosine kinase deficiency in human X-linked agammaglobulinemia. The Btk protein comprises a number of motifs, including SH1, SH2, SH3 and PH motifs, and interacts with a number of proteins in the BCR signal transduction pathway.

The present application discloses the finding that Btk binds to Mkk3b, a dual specificity kinase.

Mkk3b is a known dual specificity kinase that phosphorylates and activates p38 MAP kinase on specific threonine and tyrosine residues (Han et al., FEBS Letters 403:19-22, 1997; Ravanti et al., J. Biol. Chem. 274:37292-300, 1999). A second isoform, namely Mkk3, has similar function but is much less efficient at phosphorylating and activating p38 MAP kinase (Han et al., ibid). Mkk3b has an additional 29 amino acids at the N-terminus compared with Mkk3. Both Mkk3 and Mkk3b comprise a kinase domain, which can be further subdivided into an ATP pocket and an activation site. The activation site contains a serine at position 218, and a threonine at position 222.

Mkk3 responds to a variety of stresses such as shear stree, oxidative stress, and osmotic shock, as well as to cytokines and growth factors such as TNF, and FGF (Han et al., supra; Wysk et al., Proc. Natl Acad. Sci., 96:3763-3768, 1999; Matsumoto et al., J. Cell Biol., 156:149-160, 2002; Davis et. al., U.S. Pat. No. 5,736,381; Davis et. al., U.S. Pat. No. 5,804,427; Davis et. al. WO 96/36642). Mkk3b is activated by phosphorylation of residues serine 218 (S218) and threonine 222 (T222). Mkk3 is activated by mixed lineage kinase 1 (MLK3) (Tibbles et al., EMBO J, 15:7026-7035,1996), and apoptosis signal-regulating kinase 1 (ASK1) (Ichijo et al., Science, 275:90-94, 1997). Autophosphorylation of Mkk3 has been detected (Derijard et al., Science 267:682-685,1995) and Mkk3b is dephosphorylated by protein phosphatase 2C (Hanada et al, FEBS Letters 437:172-176, 1998). A constitutively active variant of Mkk3b which does not require phosphorylation in order to exhibit Mkk3b bioactivity has also been generated (Wang et al., J. Biol. Chem., 273:2161-2168, 1998).

Once activated, Mkk3b phosphorylates p38, a kinase involved in the inflammatory responses including the regulation of T and B cell activation and differentiation. The activation of human p38 is mediated by phosphorylation of threonine residue 180 and tyrosine residue 182 by Mkk3 and Mkk3b (Derijard et al., Science 267:682-685, 1995; Han et al., FEBS Letters 403:19-22, 1997; Moriguchi et al., J. Biol. Chem. 271:26981-8, 1996). Homozygous p38 gene inactivation in mice is lethal. Most p38 nullizygous mice die during embryogenesis; those that survive exhibit a deficit in erythropoietin expression and die early in adulthood (Tamura et al., Cell 102:221-231, 2000).

In contrast, mice deficient in Mkk3 function exhibit inflammatory, but not systemic, defects. Inactivation of the Mkk3 gene in mice has been shown to perturb the Th1 response, and Mkk3 deficient macrophages and antigen presenting cells exhibit a deficit in IL-12 induction in response stimulation with LPS or CD40L. Mkk3 nullizygous mice also exhibit a defect in interferon-gamma (IFN-γ) secretion by Th1 cells, and in proinflammatory cytokine production by fibroblasts following TNF stimulation (Lu et al., EMBO J. 18:1845-1857, 1999). Importantly, Mkk3-deficient mice are viable and fertile, exhibit no developmental defects, have no gross histological abnormalities, and exhibit normal numbers and development of B cells, T cells, monocytes, and dendritic cells.

Despite its implication in inflammatory processes, a role for Mkk3b in B cells has not been established.

SUMMARY OF THE INVENTION

The present invention provides compositions and methods for modulating lymphocyte activation. Nucleic acids and proteins which are capable of modulating lymphocyte activation are provided. Compositions and methods for the treatment of disorders related to lymphocyte activation are also provided. Prophylactics and methods for the prevention of such disorders are also provided. Also provided are compositions and methods for diagnostic and prognostic determination of such disorders. Further provided are methods of screening for bioactive agents capable of modulating lymphocyte activation.

Accordingly, in one aspect, the invention provides Mkk3b nucleic acids which are capable of modulating lymphocyte activation. In some preferred embodiments, Mkk3b nucleic acids provided herein encode Mkk3b proteins.

In some preferred embodiments, the Mkk3b nucleic acids provided herein comprise a nucleic acid sequence having at least about 85%, more preferably at least about 90%, more preferably at least about 95%, more preferably at least about 98% identity to the nucleic acid sequence set forth in SEQ ID NO:1. In a preferred embodiment, the Mkk3b nucleic acid comprises a nucleic acid sequence having at least about 95% identity to the full length nucleic acid sequence set forth in SEQ ID NO:1. In another preferred embodiment, the Mkk3b nucleic acid comprises the nucleic acid sequence set forth in SEQ ID NO:1. In a preferred embodiment, the Mkk3b nucleic acid encodes an Mkk3b protein.

Also provided herein are Mkk3b antisense nucleic acids which nucleic acids will hybridize under high stringency conditions to an Mkk3b nucleic acid comprising the nucleic acid sequence set forth in SEQ ID NO:1. Also provided are Mkk3b antisense nucleic acids which nucleic acids will hybridize under high stringency conditions to regulatory nucleic acid sequences upstream or downstream of Mkk3b encoding nucleotide sequences in Mkk3b nucleic acids. In a preferred embodiment, the Mkk3b antisense nucleic acid inhibits expression of Mkk3b protein encoded by Mkk3b nucleic acid. In a preferred embodiment, the Mkk3b antisense nucleic acid inhibits Mkk3b protein activity.

Also provided herein are small interfering RNAs comprising nucleic acid sequences having at least about 95% identity to fragments of the sequence set forth in SEQ ID NO:1. These small interfering RNAs may be used to silence Mkk3 gene expression in lymphocytes and/or APCs and thereby modulate lymphocyte activation. Preferred small interfering RNAs are about 20 base pairs in length. Preferred small interfering RNAs are less than about 30 base pairs in length, so as to elicit Mkk3-specific rather than general gene silencing effects, as is known in the art (Elbashir et al., Nature, 411:494-498, 2001; Sharp, Genes Dev., 15:485-490, 2001). In a preferred embodiment, the small interfering RNA is a single stranded RNA which is partly self complementary and capable of folding to form a short double stranded RNA.

Also provided herein are Mkk3b proteins capable of modulating lymphocyte activation.

In some preferred embodiments, the Mkk3b proteins provided herein comprise an amino acid sequence encoded by a nucleic acid sequence having at least about 85%, more preferably at least about 90%, more preferably at least about 95%, more preferably at least about 98% identity to the nucleic acid sequence set forth in SEQ ID NO:1. In a preferred embodiment, the Mkk3b protein comprises an amino acid sequence encoded by a nucleic acid sequence having at least about 95% identity to the nucleic acid sequence set forth in SEQ ID NO:1. In a preferred embodiment, the Mkk3b protein comprises an amino acid sequence encoded by a nucleic acid sequence having at least about 95% identity to the full length nucleic acid sequence set forth in SEQ ID NO:1. In another preferred embodiment, the Mkk3b protein comprises an amino acid sequence encoded by the nucleic acid sequence set forth in SEQ ID NO:1. In a preferred embodiment, the Mkk3b protein comprises an amino acid sequence encoded by the full length nucleic acid sequence set forth in SEQ ID NO:1.

In some preferred embodiments, the Mkk3b proteins comprise an amino acid sequence having at least about 85%, more preferably at least about 90%, more preferably at least about 95%, more preferably at least about 98% identity to the amino acid sequence set forth in SEQ ID NO:2. In a preferred embodiment, the Mkk3b protein comprises an amino acid sequence having at least about 95% identity to the amino acid sequence set forth in SEQ ID NO:2. In a preferred embodiment, the Mkk3b protein comprises an amino acid sequence having at least about 95% identity to the full length amino acid sequence set forth in SEQ ID NO:2. In another preferred embodiment, the Mkk3b protein comprises the amino acid sequence set forth in SEQ ID NO:2. In a preferred embodiment, the Mkk3b protein comprises the full length amino acid sequence set forth in SEQ ID NO:2.

Preferably, an Mkk3b protein of the present invention also possesses one or more Mkk3b bioactivities described herein.

In one aspect of the invention, expression vectors are provided. The expression vectors comprise one or more Mkk3b nucleic acids provided herein operably linked to regulatory sequences recognized by a host cell transformed with the expression vector. Further provided herein are host cells comprising expression vectors and/or Mkk3b nucleic acids provided herein. Also provided are processes for producing Mkk3b protein comprising culturing a host cell provided herein under conditions suitable for expression of the Mkk3b protein. In one embodiment, the process includes recovering and/or isolating the Mkk3b protein.

The present invention also provides isolated polypeptides which specifically bind to an Mkk3b protein. In one aspect, the polypeptide is an antibody. In a preferred aspect, the polypeptide is a monoclonal antibody.

Also provided herein are methods of screening for a bioactive agent capable of binding to the Mkk3b protein and modulating lymphocyte activation. In some embodiments, the methods comprise combining an Mkk3b protein and a candidate bioactive agent and determining the binding of candidate agent to Mkk3b protein. In one embodiment, the method involves identifying the candidate agent.

Also provided herein are methods of screening for a bioactive agent capable of interfering with the binding of an Mkk3b protein to a binding partner and modulating lymphocyte activation. In some preferred embodiments, the methods comprise combining a candidate bioactive agent, an Mkk3b protein, and an Mkk3b binding partner which will bind to Mkk3b in the absence of candidate agent, and determining the binding of Mkk3b to its binding partner in the presence of candidate bioactive agent. In a preferred embodiment, the Mkk3b binding partner is Btk, p38 MAPK, or protein phosphatase 2C (PP2C). In a preferred embodiment, the method involves determining the binding of Mkk3b to its binding partner in the presence and absence of a candidate bioactive agent. In one embodiment, Mkk3b and Mkk3b binding partner are combined first, although other orders of addition can be done. In a preferred embodiment, the method involves identifying the candidate bioactive agent.

Also provided herein are methods of screening for a bioactive agent capable of increasing the binding of an Mkk3b protein to a ligand, and modulating lymphocyte activation. In some preferred embodiments, the methods comprise combining a candidate bioactive agent, an Mkk3b protein, and an Mkk3b binding partner which will bind to Mkk3b in the absence of candidate bioactive agent and determining the binding of Mkk3b to binding partner in the presence of candidate bioactive agent. In a preferred embodiment, the Mkk3b binding partner is Btk, p38 MAPK, or PP2C. In a preferred embodiment, the method involves determining the binding of Mkk3b to binding partner in the presence and absence of candidate bioactive agent. In one embodiment, Mkk3b and Mkk3b binding partner are combined first. In a preferred embodiment, the method involves identifying the candidate bioactive agent.

Also provided herein are methods of screening for a bioactive agent capable of modulating the activity of an Mkk3b protein and thus modulating lymphocyte activation. In some preferred embodiments, the methods comprise contacting a candidate bioactive agent to a cell comprising a recombinant Mkk3b nucleic acid and expressing Mkk3b protein. In some preferred embodiments, the methods comprise contacting a library of candidate bioactive agents to a plurality of cells comprising a recombinant Mkk3b nucleic acid and expressing Mkk3b protein.

In other embodiments, the methods comprise contacting a sample of Mkk3b protein with a candidate bioactive agent and determining Mkk3b activity in the presence of the candidate bioactive agent. In a preferred embodiment, a cell-free Mkk3b sample is used, such as a cell extract. In a preferred embodiment, Mkk3b activity is determined in the presence and absence of a candidate bioactive agent.

In a preferred embodiment, Mkk3b activity is determined by measuring Mkk3b kinase activity.

In another preferred embodiment, Mkk3b activity is determined by measuring Mkk3b phosphorylation.

In another preferred embodiment, Mkk3b activity is determined by measuring p38 MAPK activity.

In another preferred embodiment, Mkk3b activity is determined by measuring p38 MAPK phosphorylation.

In some preferred embodiments, the methods comprise expressing recombinant Mkk3b nucleic acid in a lymphocyte or antigen presenting cell (APC), contacting the expressing cell with a candidate bioactive agent, and determining the level of expression of a surface marker which is normally associated with lymphocyte activation, in the presence of the candidate bioactive agent. In a preferred embodiment, the level of surface marker expression is determined in the presence and absence of the candidate bioactive agent. In a preferred embodiment, the surface marker is selected from the group consisting of CD69, CD80 and CD25. In a preferred embodiment, determining the level of surface marker expression is done using a FACS machine, which provides for the optional sorting of cells based on the level of surface marker expression.

In a preferred embodiment, B-lymphocytes are used and the method additionally involves stimulating the CD40 protein complex or the B-cell receptor (BCR) in B-lymphocytes prior to contacting the cells with a candidate bioactive agent. In another preferred embodiment, B-lymphocytes are contacted with the candidate bioactive agent prior to BCR or CD40 stimulation. Preferably, BCR stimulation involves the use of anti-IgM antibody, while CD40 stimulation preferably involves the use of CD40L or anti-CD40 antibody.

In another preferred embodiment, APCs are used and the method additionally involves stimulating the CD40 protein complex in APCs prior to contacting APCs with a candidate bioactive agent. In another preferred embodiment, APCs are contacted with candidate agent prior to CD40 stimulation. Preferably, CD40 stimulation involves the use of CD40L or an anti-CD40 antibody.

In some preferred embodiments, the methods comprise expressing recombinant Mkk3b nucleic acid in a lymphocyte, contacting the expressing cell with a candidate bioactive agent, and determining the level of activity of a promoter which activity normally correlates with lymphocyte activation, in the presence of the candidate bioactive agent. In a preferred embodiment, the level of promoter activity is determined in the presence and absence of the candidate bioactive agent. In a preferred embodiment the promoter is responsive to the nuclear factor activated in T cells (NFAT) transcription factor, e.g., the IL-2 gene promoter.

In a preferred embodiment, T-lymphocytes are used and the method additionally involves stimulating the TCR in T-lymphocytes prior to contacting the cells with a candidate bioactive agent. In another preferred embodiment, T-lymphocytes are contacted with a candidate bioactive agent prior to TCR stimulation. Preferably, TCR stimulation involves the use of an anti-CD3 antibody.

In a preferred embodiment, B-lymphocytes are used and the method additionally involves stimulating the BCR in B-lymphocytes prior to contacting the cells with a candidate bioactive agent. In another preferred embodiment, B-lymphocytes are contacted with a candidate bioactive agent prior to BCR stimulation. Preferably, BCR stimulation involves the use of an anti-IgM antibody.

In some preferred embodiments, the methods comprise expressing Mkk3b nucleic acid in a lymphocyte or APC, contacting the expressing cell with a candidate bioactive agent, and determining the activity of p38 MAPK (used herein interchangeably with p38 and p38 MAP kinase). In a preferred embodiment, the method involves determining the phosphorylation of p38, preferably the threonine and/or tyrosine phosphorylation of p38, preferably the phosphorylation of T180 and Y182 of human p38. In a preferred embodiment, anti-phospho-p38 antibody which specifically recognizes phosphorylated p38 is used to detect phosphorylated p38. In a preferred embodiment, determining p38 phosphorylation is done using a FACS machine, which provides for the optional sorting of cells based on the level of p38 phosphorylation.

In another preferred embodiment, determining the activity of p38 involves performing a kinase assay using a substrate which is capable of being phosphorylated by p38. In one embodiment, a kinase assay is done using ATF2 as such a p38 substrate.

In a preferred embodiment, T-lymphocytes are used and the method additionally involves stimulating the TCR in T-lymphocytes prior to contacting the cells with a candidate bioactive agent. In another preferred embodiment, T-lymphocytes are contacted with a candidate bioactive agent prior to TCR stimulation. Preferably, TCR stimulation involves the use of an anti-CD3 antibody.

In a preferred embodiment, B-lymphocytes are used and the method additionally involves stimulating the CD40 protein complex or the BCR in B-lymphocytes prior to contacting the cells with a candidate bioactive agent. In another preferred embodiment, B-lymphocytes are contacted with a candidate agent prior to BCR or CD40 stimulation. Preferably, BCR stimulation involves the use of anti-IgM antibody, while CD40 stimulation preferably involves the use of CD40L or an anti-CD40 antibody.

In one embodiment, antigen presenting cells (APCs) are used and the method additionally involves stimulating the CD40 protein complex in APCs prior to contacting APCs with candidate bioactive agent. In another preferred embodiment, APCs are contacted with candidate agent prior to CD40 stimulation. Preferably, CD40 stimulation involves the use of CD40L or an anti-CD40 antibody.

Additional methods of screening for a bioactive agent capable of modulating lymphocyte activation are provided herein. In some preferred embodiments, the methods comprise screening for an agent capable of binding to an Mkk3b protein, using assays provided herein. In other preferred embodiments, the methods comprise screening for an agent capable of modulating the binding of an Mkk3b protein with a binding ligand, using assays provided herein. In other preferred embodiments, the methods comprise screening for an agent capable of modulating Mkk3b protein activity, using assays provided herein.

In some preferred embodiments, the methods comprise contacting a sample of Mkk3b protein with a candidate bioactive agent, detecting a change in the kinase activity of Mkk3b in the presence of the candidate bioactive agent, and optionally further contacting the candidate agent to a lymphocyte, inducing activation of the lymphocyte, and determining the activation of the lymphocyte in the presence of the candidate agent. A change in the kinase activity of Mkk3b in the presence of the candidate agent indicates that the candidate agent is capable of modulating lymphocyte activation. A subsequent, optionally measured change in the activation of a lymphocyte in the presence of the candidate bioactive agent confirms the activity of the candidate bioactive agent as a modulator of lymphocyte activation.

In a preferred embodiment, B-lymphocytes are used and the method additionally involves stimulating the CD40 protein complex or the BCR in B-lymphocytes prior to contacting the cells with a candidate bioactive agent. In another preferred embodiment, B-lymphocytes are contacted with a candidate agent prior to BCR or CD40 stimulation. Preferably, BCR stimulation involves the use of anti-IgM antibody, while CD40 stimulation preferably involves the use of CD40L or an anti-CD40 antibody.

In another preferred embodiment, T-lymphocytes are used and the method additionally involves stimulating the TCR in T-lymphocytes prior to contacting the cells with a candidate bioactive agent. In another preferred embodiment, T-lymphocytes are contacted with a candidate bioactive agent prior to TCR stimulation. Preferably, TCR stimulation involves the use of an anti-CD3 antibody.

In a preferred embodiment, determining lymphocyte activation involves measuring the level of expression of at least one surface marker in the presence of the candidate bioactive agent. The surface marker(s) used has an expression profile that correlates with lymphocyte activation in the absence of the candidate bioactive agent. In a preferred embodiment, the surface marker is selected from the group consisting of CD69, CD80 and CD25. In a preferred embodiment, surface marker expression is measured in the presence of the candidate bioactive agent. In a preferred embodiment, measuring the level of expression of at least one surface marker is done using a FACS machine, which provides for the optional sorting of cells based on the level of surface marker expression.

In another preferred embodiment, determining lymphocyte activation involves measuring the level of activity of a promoter, which activity correlates with lymphocyte activation in the absence of a candidate bioactive agent. In a preferred embodiment, the promoter is responsive to NFAT activity, e.g., the IL-2 promoter. In a preferred embodiment, the promoter is operatively linked to a reporter gene which is expressed to produce a detectable product. In a preferred embodiment, the level of expression of reporter gene-encoded detectable product is measured to determine promoter activity. In a preferred embodiment, the reporter gene-encoded detectable product is detected using an antibody that specifically binds to the reporter gene-encoded detectable product. In a preferred embodiment, measuring reporter gene-encoded detectable product is done using a FACS machine, which provides for the optional sorting of cells based on promoter activity.

In another preferred embodiment, determining lymphocyte activation involves determining Mkk3b activity. In a preferred embodiment, Mkk3b activity is determined by measuring Mkk3b phosphorylation. In a preferred embodiment, Mkk3b phosphorylation is measured using an anti phospho-Mkk3b antibody, which antibody specifically binds to phosphorylated Mkk3b protein. In another preferred embodiment, Mkk3b activity is determined by assaying Mkk3b kinase activity.

In another preferred embodiment, determining lymphocyte activation involves determining p38 MAPK activity. In a preferred embodiment, p38 MAPK activity is determined by measuring p38 MAPK phosphorylation. In a preferred embodiment, p38 MAPK phosphorylation is measured using an anti phospho-p38 MAPK antibody, which antibody specifically binds to phosphorylated p38 MAPK protein. In another preferred embodiment, p38 MAPK activity is determined by assaying p38 MAPK kinase activity.

Also provided herein are methods of screening for bioactive agents capable of modulating the activity of p38 MAPK. In some preferred embodiments, the methods comprise expressing Mkk3b nucleic acid in a lymphocyte or antigen presenting cell (APC), which cell also expresses the surface antigen CD40, contacting the cell with a candidate bioactive agent, stimulating CD40 in the cell, and determining the expression of CD80 in the cell. In a preferred embodiment, determining CD80 expression involves the use of anti-CD80 antibody. In a preferred embodiment, determining CD80 expression is done using a FACS machine, which provides for the optional sorting of cells based on CD80 expression.

In a preferred embodiment, B lymphocytes are used and the method involves stimulating the CD40 protein complex in B lymphocytes prior to contacting the cells with a candidate bioactive agent. In another preferred embodiment, B lymphocytes are contacted with a candidate bioactive agent prior to CD40 stimulation. Preferably, CD40 stimulation involves the use of CD40L or an anti-CD40 antibody.

In another preferred embodiment, antigen presenting cells (APCs) are used and the method involves stimulating the CD40 protein complex in APCs prior to contacting the cells with a candidate bioactive agent. In another preferred embodiment, APCs are contacted with a candidate bioactive agent prior to CD40 stimulation. Preferably, CD40 stimulation involves the use of CD40L or an anti-CD40 antibody.

The present invention also provides methods for modulating lymphocyte activation.

In some preferred embodiments, the methods comprise introducing into a lymphocyte an agonist or antagonist of Mkk3b activity. In a preferred embodiment, the agonist or antagonist of Mkk3b activity is a small interfering RNA capable of silencing the expression of an Mkk3b gene encoding an Mkk3b protein. In another preferred embodiment, the agonist or antagonist of Mkk3b activity is an anti-Mkk3b antibody which specifically binds to an Mkk3b protein. In another preferred embodiment, the agonist or antagonist of Mkk3b activity is a small molecule chemical compound. In another preferred embodiment, the agonist or antagonist of Mkk3b activity is a recombinant nucleic acid encoding a constitutively active Mkk3b protein. In another preferred embodiment, the agonist or antagonist of Mkk3b activity is a recombinant nucleic acid encoding a kinase dead Mkk3b protein (e.g., a dominant negative, in the case of an antagonist).

Also provided herein are methods for modulating CD80 expression in a lymphocyte and/or APC.

In some embodiments, the methods comprise introducing into a lymphocyte and/or APC an agonist or antagonist of p38 MAPK activity.

In other embodiments, the methods comprise introducing into a lymphocyte and/or APC an agonist or antagonist of Mkk3b activity. In a preferred embodiment, the agonist or antagonist of Mkk3b activity is a small interfering RNA capable of silencing the expression of an Mkk3b gene encoding an Mkk3b protein. In another preferred embodiment, the agonist or antagonist of Mkk3b activity is an anti-Mkk3b antibody which specifically binds to an Mkk3b protein. In another preferred embodiment, the agonist or antagonist of Mkk3b activity is an anti-Mkk3b antibody which specifically binds to an Mkk3b protein. In another preferred embodiment, the agonist or antagonist of Mkk3b activity is a small molecule chemical compound.

Compositions and methods for the modulation of lymphocyte activation are also provided herein. These include proteins, nucleic acids and small molecule chemical compositions. Some of these compositions find use as immunosuppressants. Some of these compositions find use as prophylactics and therapeutics for the prevention and treatment of diseases and undesired physiological states mediated by lymphocyte activation. In a preferred embodiment, provided herein are small molecule chemical compositions useful as immunosuppressants. In a preferred embodiment, provided herein are small molecule chemical compositions useful for the prevention and treatment of acute inflammatory disorders, chronic inflammatory disorders, autoimmune disorders, transplant rejection, and T cell and B cell cancers.

BRIEF DESCRIPTION OF THE DRAWINGS

FIG. 5 shows the nucleic acid sequence (SEQ ID NO:1) of human Mkk3b which is found at Genbank Accession No. D87116. The translation start codon at position 58 is bolded and underlined. The termination codon at 1101 is also bolded and underlined.

FIG. 6 shows the amino acid sequence (SEQ ID NO:2) of human Mkk3b which is found at Genbank Accession No. BAA13248.

FIG. 11 describes the optimization of B cell stimulation by a variety of agents. The level of expression of a variety of indicators of B cell activation in response to activation with the various agents is given as a fold induction over unstimulated cells.

DETAILED DESCRIPTION OF THE INVENTION

Figure 1:
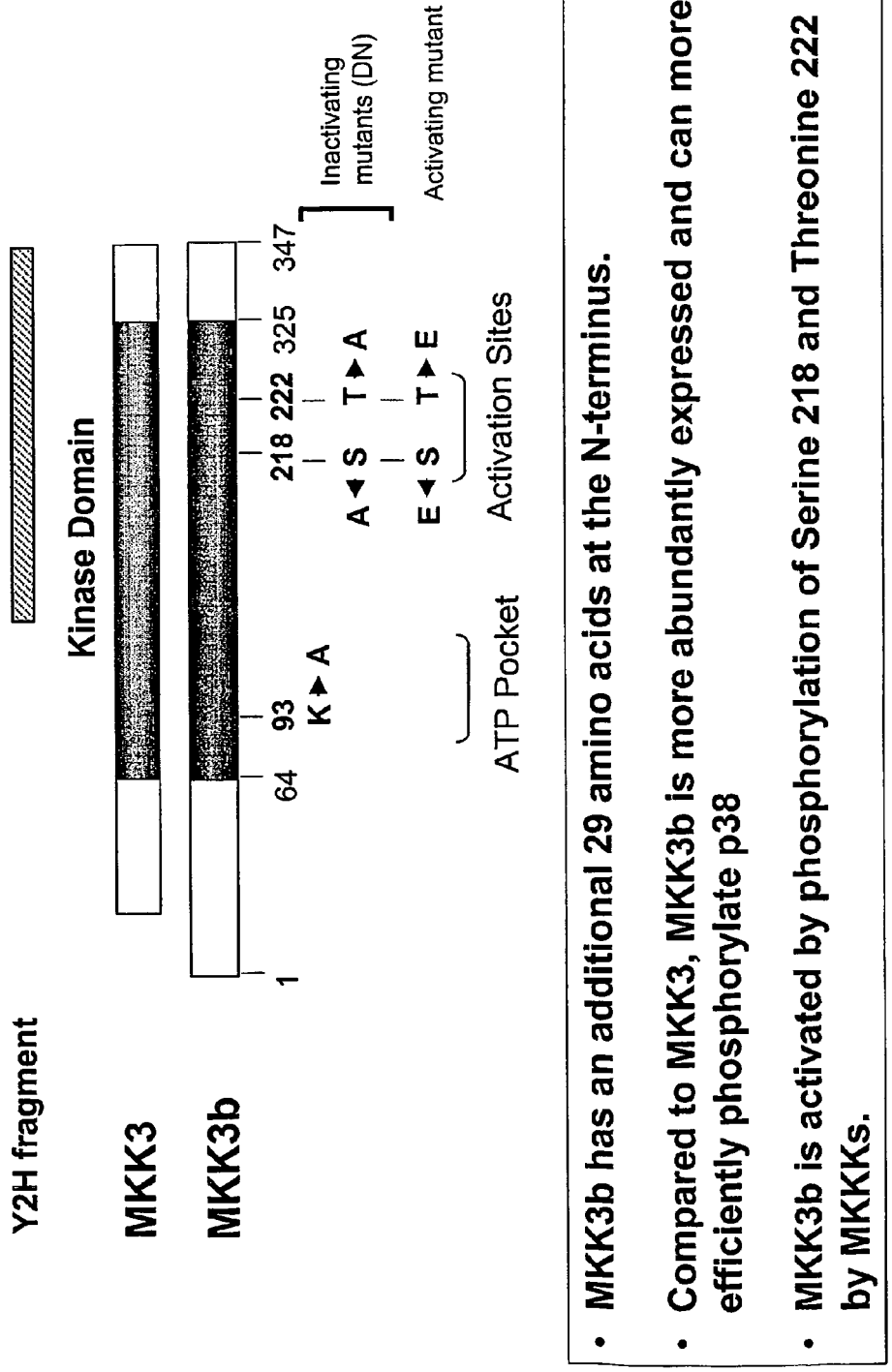
FIG. 1 is a schematic diagram showing the structural relationship between Mkk3b and Mkk3. The figure shows the location of the kinase domain in Mkk3b and Mkk3 (from residues 64-325 in Mkk3b) as well as the relative positions of the ATP pocket and activation regulatory sites within the kinase domain. Mkk3b has an additional 29 amino acids at the N-terminus as compared to Mkk3, and the remainder of the sequence is identical to Mkk3. Mkk3b is a more abundantly expressed than Mkk3 and is more efficient at phosphorylating p38. The figure shows the location of the ATP pocket domain and the activation sites of Mkk3b. Mkk3b is activated by phosphorylation on serine 218 and threonine 222. In addition, the figure shows the sequence mutations of inactive and constitutively active mutants. Mutation S-A at position 218 and T-A at position 222 in the activation site are mutations producing inactive dominant negative mutants. Similarly, mutation K-A at residue 93 in the ATP pocket is an inactivating mutation. Conversely, mutation S-E at position 218 and T-E at position 222 in the activation site are activating mutations.
Figure 2:
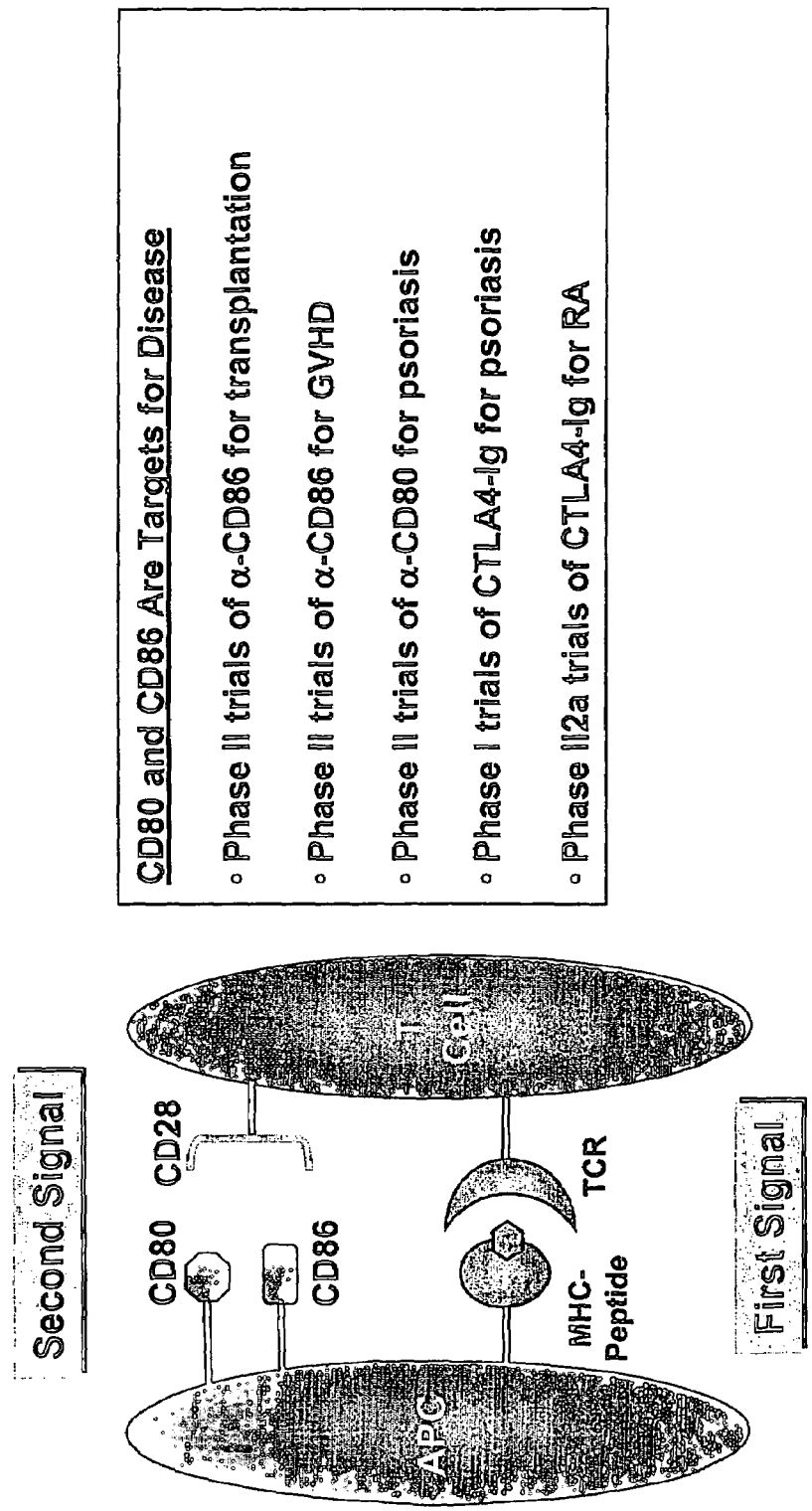
FIG. 2 is a schematic diagram showing the importance of CD80 and CD86 costimulation. APC denotes an antigen presenting cell. T cell denotes a T lymphocyte.

The present invention provides compositions and methods for modulating lymphocyte activation. Nucleic acids and proteins which are capable of modulating lymphocyte activation are provided. Compositions and methods for the treatment of disorders related to lymphocyte activation are also provided. Prophylactics and methods for the prevention of such disorders are also provided. Also provided are compositions and methods for diagnostic and prognostic determination of such disorders. Further provided are assays for the identification of bioactive agents capable of modulating lymphocyte activation.

In accordance with these objectives, in one aspect, the present invention provides Mkk3b nucleic acids capable of modulating lymphocyte activation. Also in accordance with these objectives, in another aspect, the invention provides Mkk3b proteins capable of modulating lymphocyte activation.

Nucleic acids are defined below. The Mkk3b nucleic acids have at least about 85%, more preferably at least about 90%, more preferably at least about 95%, more preferably at least about 98% identity to the nucleic acid sequence set forth in SEQ ID NO:1. In a preferred embodiment, the Mkk3b nucleic acid comprises a nucleic acid sequence having at least about 95% identity to the nucleic acid sequence set forth in SEQ ID NO:1. In another preferred embodiment, the Mkk3b nucleic acid comprises the nucleic acid sequence set forth in SEQ ID NO:1. In a preferred embodiment, the Mkk3b nucleic acid encodes an Mkk3b protein.

Also provided herein are Mkk3b antisense nucleic acids which nucleic acids will hybridize under high stringency conditions to an Mkk3b nucleic acid comprising the nucleic acid sequence set forth in SEQ ID NO:1. In a preferred embodiment, the Mkk3b antisense nucleic acids hybridize under high stringency conditions to regulatory nucleic acid sequences upstream or downstream of Mkk3b encoding nucleotide sequences in Mkk3b nucleic acids. In a preferred embodiment, the Mkk3b antisense nucleic acid inhibits expression of Mkk3b protein encoded by Mkk3b nucleic acid. In a preferred embodiment, the Mkk3b antisense nucleic acid inhibits Mkk3b protein activity.

Also provided herein are small interfering RNAs comprising nucleic acid sequences having at least about 95% identity to fragments of the sequence set forth in SEQ ID NO:1. These small interfering RNAs may be used to silence Mkk3 gene expression in lymphocytes and/or APCs and thereby modulate lymphocyte activation. Preferred small interfering RNAs are about 20 base pairs in length. Preferred small interfering RNAs are less than about 30 base pairs in length, so as to elicit Mkk3-specific rather than general gene silencing effects, as is known in the art (Elbashir et al., Nature, 411:494-498, 2001; Sharp, Genes Dev., 15:485-490, 2001; both expressly incorporated herein by reference). In a preferred embodiment, the small interfering RNA is a single stranded RNA which is partly self complementary and capable of folding to form a short double stranded RNA.

The present invention also provides Mkk3b proteins which are capable of modulating lymphocyte activation. Proteins are defined below.

In a preferred embodiment, the Mkk3b protein comprises an amino acid sequence encoded by a nucleic acid sequence having at least about 85%, more preferably at least about 90%, more preferably at least about 95%, more preferably at least about 98% identity to the nucleic acid sequence set forth in SEQ ID NO:1. In a preferred embodiment, the Mkk3b protein comprises an amino acid sequence encoded by a nucleic acid sequence having at least about 95% identity to the full length nucleic acid sequence set forth in SEQ ID NO:1. In a preferred embodiment, the Mkk3b protein comprises an amino acid sequence encoded by the nucleic acid sequence set forth in SEQ ID NO:1.

In some preferred embodiments, Mkk3b proteins comprise an amino acid sequence having at least about 85%, more preferably at least about 90%, more preferably at least about 95%, more preferably at least about 98% identity to the amino acid sequence set forth in SEQ ID NO:2. IN a preferred embodiment, the Mkk3b protein comprises an amino acid sequence having at least about 95% identity to the full length amino acid sequence set forth in SEQ ID NO:2. In a preferred embodiment, the Mkk3b protein comprises the amino acid sequence set forth in SEQ ID NO:2.

Homology and identity to the Mkk3b nucleic acid set forth in SEQ ID NO:1 and the Mkk3b amino acid sequence encoded thereby in SEQ ID NO:2 can be determined as described below. In one embodiment, homology and identity are determined by performing a Blastp search in Genbank's non-redundant protein database using default parameters. In another embodiment, homology and identity are determined using the following database and parameters: Database: Non-redundant GenBank CDS translations+PDB+SwissProt+Spupdate+PIR; Lambda of 0.316, K of 0.133 and H of 0; Gapped Lambda of 0.27, K of 0.047, and H of 4.94e-324; Matrix is BLOSUM62; Gap Penalities: Existence: 11, Extension: 1.

Preferably, the Mkk3b protein also possesses one or more Mkk3b bioactivities described herein.

An Mkk3b protein of the present invention may be identified in several ways. "Protein" in this sense includes proteins, polypeptides, and peptides. An Mkk3b protein may be identified by possession of Mkk3b protein characteristics. In a preferred embodiment, an Mkk3b protein of the present invention comprises a kinase domain which in turn comprises an ATP pocket with a critical lysine residue such as lysine 93 in SEQ ID NO:2 as shown in FIG. 1, and two regulatory sites capable of being phosphorylated such as serine 218 and threonine 222 of SEQ ID NO:2 as shown in FIG. 1.

In a preferred embodiment, the Mkk3b protein has one or more of the following characteristics: ability to bind to Btk; ability to bind to PP2C; ability to be dephosphorylated by PP2C, preferably on residues corresponding to S218 and T222 as shown in FIG. 1; ability to bind to p38 MAPK; ability to phosphorylate p38 MAPK, preferably human p38 MAPK, preferably on T180 and Y182; ability to modulate the activity of p38 MAPK; ability to modulate lymphocyte activation; ability to modulate CD69 expression in B cells; ability to modulate CD80 expression in B cells and APCs; ability to modulate CD25 expression in B cells and APCs; ability to modulate T cell activation; ability to modulate B cell activation; ability to modulate NFAT activity in T cells and B cells; ability to modulate CD40- and BCR-induced B cell activation; ability to modulate CD40- and BCR-induced expression of CD80; ability to modulate CD40- and BCR-induced expression of CD25; ability to be phosphorylated on threonine and serine in response to UV, osmotic shock, cytokine stimulation, oxidative stress, BCR activation, TCR activation, or CD40 activation, preferably on residues in the kinase domain and corresponding to S218 and T222 as shown in FIG. 1. These characteristics are generally referred to herein as "Mkk3b protein activities" or "Mkk3b biological activities".

In a preferred embodiment, the Mkk3b protein binds to Btk, or a derivative thereof, e.g. phosphorylated Btk and/or complexed Btk. Btk is a known non-receptor tyrosine kinase involved in the BCR signaling pathway and B cell development. Binding and activity assays are described below. Binding assays include the yeast two hybrid assay described below and co-immunoprecipitation assays known in the art; for example see *Current Protocols in Protein Science*, John Wiley and Sons, J. E. Coligan et. al. editors, ISBN 047 1140988; published August 1995, edited September 2001, Chapter 19 "Identification of Protein Interactions", expressly incorporated herein by reference. References herein to Btk include active derivatives.

In a preferred embodiment, the Mkk3b protein binds to p38 MAPK, or a derivative thereof, e.g. phosphorylated p38 and/or complexed p38. p38 MAPK is a known protein serine/threonine kinase involved in intracellular signal transduction implicated in inflammatory diseases (for review, see Herlaar et al., Mol. Med. Today, 5:439-444, 1999). References herein to p38 MAPK include active derivatives.

In a further preferred embodiment, Mkk3b phosphorylates p38 MAPK. In a further preferred embodiment, Mkk3b protein activates p38 MAPK. Preferably, Mkk3b protein binds to human p38 MAPK, phosphorylates human p38 MAPK on T180 and Y182, and activates human p38 MAPK. Phosphorylation assays are described below and are known in the art, for example see *Current Protocols in Protein Science*, J. E. Coligan et. al. editors, supra, Chapter 13 "Post-translational modification: phosphorylation and phosphatases", expressly incorporated herein by reference.

In a preferred embodiment, the Mkk3b protein comprises a kinase domain which comprises an ATP binding pocket, as shown in FIG. 1. In a preferred embodiment, Mkk3b protein binds ATP in its kinase domain. Preferably binding to ATP requires the presence of a critical lysine residue within the ATP pocket of the kinase domain of Mkk3b, as shown in FIG. 1.

In a preferred embodiment, activation of Mkk3b in T cells induces and/or enhances T cell activation.

By T cell herein is meant T lymphocyte, including T lymphocyte like cells, such as a T lymphocyte-derived cell line, e.g., Jurkat T cells, or primary T cell cancer cells.

In a preferred embodiment, activation of Mkk3b in B cells induces and/or enhances B cell activation.

By B cell herein is meant B lymphocyte, including B lymphocyte-like cells, such as a B lymphocyte derived cell line, e.g., BJAB cells, or primary B cell cancer cells.

Importantly, the B and T cells used in the invention may be used in the methods provided herein to screen for agents that are effective at modulating activation of B lymphocytes and T lymphocytes, preferably human B lymphocytes and T lymphocytes. However, other mammalian B and T cells can be used, including, but not limited to, primate and rodent cells.

In a preferred embodiment, Mkk3b overexpression induces and/or increases the activity of the transcription factor nuclear factor activated in T-cells (NFAT) in B and T cells.

Activation of the protein phosphatase calcineurin in lymphocytes regulates the phosphorylation of NFAT, and thereby regulates nuclear import of NFAT and its ability to regulate transcription. The expression of many factors involved in lymphocyte activation, including cytokines (such as IL-2) and cell surface molecules (eg. CD40L) lies downstream of NFAT activation. (see Klee et al., J Biol Chem., 273:13367, 1998; Stankunas et al., Cold Spring Harbor Symposia Quant. Biol., 64: 505-516, 1999).

In a preferred embodiment, Mkk3b overexpression induces and/or increases CD69 expression in B lymphocytes.

CD69 is a transmembrane glycoprotein which is well known as a very early lymphocyte activation antigen. CDD69 plays a role in signal transduction and has been implicated in the pathogenesis of rheumatoid arthritis, chronic inflammatory diseases, asthma, and aquired immunodeficiency syndrome (Marzio et al., Immunopharmacol. Immunotoxicol., 21:565-582, 1999.

In a preferred embodiment, Mkk3b overexpression enhances the activation of T cells by TCR stimulation, for example TCR stimulation as by the use of anti-CD3 antibody.

In a preferred embodiment, Mkk3b overexpression enhances the induction of NFAT activity in T cells by TCR stimulation, for example TCR stimulation as by the use of anti-CD3 antibody.

In a preferred embodiment, Mkk3b overexpression enhances the activation of B cells by BCR stimulation, for example BCR stimulation as by the use of anti-IgM antibody.

In a preferred embodiment, Mkk3b overexpression enhances the induction of NFAT activity in B cells by BCR stimulation, for example BCR stimulation as by the use of anti-IgM antibody.

In a preferred embodiment, Mkk3b overexpression enhances the induction of CD69 expression in B cells by BCR stimulation, for example BCR stimulation as by the use of anti-IgM antibody.

In a preferred embodiment, Mkk3b overexpression enhances the induction of CD80 expression in B-cells by CD40 stimulation, for example CD40 stimulation as by the use of CD40L.

CD40 and CD40 protein complex are used interchangeably herein. The CD40 protein complex is a homodimer, and belongs to the tumor necrosis factor-receptor family. CD40 is constitutively expressed on B cells. CD40 binds to CD40L (also known as CD154), which is expressed on the surface of helper T cells after activation by antigen and costimulators. CD40L is a homotrimer protein complex (*Cellular and Molecular Immunology*, 4$^{th}$ Edition, 2000, Abbas et. al., W. B. Saunders, ISBN 0-7216-8233-2; incorporated herein by reference).

In a preferred embodiment, Mkk3b overexpression enhances the induction of CD80 expression in APCs by CD40 stimulation, for example CD40 stimulation as by the use of CD40L.

In a preferred embodiment, Mkk3b overexpression enhances the induction of CD25 expression in B-cells by CD40 stimulation, for example CD40 stimulation as by the use of CD40L.

In a preferred embodiment, Mkk3b overexpression enhances the induction of CD25 expression in APCs by CD40 stimulation, for example CD40 stimulation as by the use of CD40L.

In a preferred embodiment, Mkk3b overexpression enhances the induction of CD69 expression and NFAT activity in B cells by BCR stimulation, and the induction of NFAT activity in T cells by TCR stimulation, but not the induction of CD69 expression in T cells by TCR stimulation.

In a preferred embodiment, Mkk3b overexpression potentiates BCR-induced NFAT activation and CD69 upregulation but not IgH promoter activation in BJAB cells.

By IgH promoter herein is meant immunoglobulin heavy chain gene promoter construct. Especially preferred is a construct comprising Eµ and 3'α enhancer elements (for example, see Lieberson et al. EMBO J., 14:6229-6238, 1995, incorporated herein by reference).

In a preferred embodiment, Mkk3b overexpression enhances ionomycin induced induction of NFAT activity in lymphocytes.

In a preferred embodiment, Mkk3b overexpression enhances p38 MAPK activation by BCR and/or CD40 stimulation in B cells.

In a preferred embodiment, Mkk3b overexpression enhances p38 MAPK activation by TCR stimulation in T cells.

In one aspect, the present invention provides small molecule chemical compounds which are Mkk3b agonists and mimic the effects of Mkk3b overexpression. In a preferred embodiment, the small molecule chemical compound is identified by a screening method provided herein.

In another aspect, the present invention provides small molecule chemical compounds which are Mkk3b antagonists, which have effects opposite to those observed with Mkk3b overexpression. In a preferred embodiment, the small molecule chemical compound is identified by a screening method provided herein. Such compounds find use as immunosuppressants.

By immunosuppressant is meant an agent that suppresses the body's ability to react to an antigen.

In a preferred embodiment, Mkk3b acts downstream of BCR, TCR, and CD40 stimulation, but upstream of p38, to induce activation and NFAT activity in B cells and T cells, to induce CD69 expression in B cells, and to induce CD80 and CD25 expression in B cells and APCs.

In a preferred embodiment, Mkk3b is activated by BCR and CD40 stimulation in B cells and CD40 stimulation in APCs. In a preferred embodiment, Mkk3b activation in B cells and APCs induces CD80 and/or CD25 upregulation. Preferably, such induction of CD80 and/or CD25 by Mkk3b is p38 MAPK-dependent.

In a preferred embodiment, Mkk3b is activated by BCR and CD40 stimulation in B cells and Mkk3b activation in B cells induces CD69 expression. Preferably, such induction of CD69 expression is p38 MAPK-dependent.

In a preferred embodiment, Mkk3b is activated by TCR stimulation in T cells and BCR stimulation in B cells. In a preferred embodiment, Mkk3b activation induces NFAT activity in T and B lymphocytes and activation of T and B lymphocytes.

In one aspect, constitutively active isoforms of Mkk3b are provided. Constitutively active means that the Mkk3b isoform has at least one MKK3B bioactivity in the absence of phosphorylation on serine and threonine residues corresponding to serine 218 and threonine 222 in FIG. 1, or in the absence of being activated by BCR stimulation, TCR stimulation, CD40 stimulation, or other activating stimulus. In a preferred embodiment, the present invention provides constitutively active variants of Mkk3b which comprise activating mutations at regulatory serine and threonine residues corresponding to serine 218 and threonine 222 in FIG. 1. In a preferred embodiment, the constitutively active Mkk3b variant comprises S218E and T222E mutations as described in FIG. 1.

In one aspect, constitutively inactive isoforms of Mkk3b are provided. By constitutively inactive is meant lacking at least one Mkk3b activity described herein. For example, in a preferred embodiment, the present invention provides kinase inactive Mkk3b variants comprising a K93A mutation in the ATP binding pocket of the kinase domain as shown in FIG. 1. In another preferred embodiment, the present invention provides inactive Mkk3b variants comprising S218A and T222A mutations in the kinase domain as shown in FIG. 1.

In one embodiment, Mkk3b nucleic acids and Mkk3b proteins can be initially identified by substantial nucleic acid and amino acid sequence identity or similarity to the sequences provided herein. In a preferred embodiment, Mkk3b nucleic acids and Mkk3b proteins have sequence identity or similarity to the sequences provided herein as described below and one or more Mkk3b bioactivities. Such sequence identity or similarity can be based upon the overall nucleic acid or amino acid sequence.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., *Methods in Enzymology*, 266: 460-480 (1996)]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the longer sequence in the aligned region. The longer sequence is the one having the most actual residues in the aligned region (gaps introduced by WU-Blast-2 to maximize the alignment score are ignored).

In a similar manner, percent (%) nucleic acid sequence identity" with respect to the coding sequence of the polypeptides identified herein is defined as the percentage of nucleotide residues in a candidate sequence that are identical with the nucleotide residues in the coding sequence of the Mkk3b protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of 0, which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

Mkk3b proteins of the present invention may be shorter or longer than the amino acid sequence encoded by the nucleic acid sequence shown in SEQ ID NO:1. Thus, in a preferred embodiment, included within the definition of Mkk3b proteins are portions or fragments of the amino acid sequences encoded by the nucleic acid sequences provided herein. In one embodiment herein, fragments of Mkk3b proteins are considered Mkk3b proteins if a) they share at least one antigenic epitope; b) have at least the indicated sequence identity; c) and preferably have Mkk3b protein activity (one or more Mkk3b characteristics) as further defined herein. In one embodiment, fragments of Mkk3b proteins are considered Mkk3b proteins if: a) they have at least the indicated sequence identity; and b) they possess dual specificity kinase activity, particularly tyrosine and threonine kinase activity. In some cases, where the sequence is used diagnostically, that is, when the presence or absence of Mkk3b nucleic acid is determined, only the indicated sequence identity is required. The nucleic acids of the present invention may also be shorter or longer than SEQ ID NO:1. The nucleic acid fragments include any portion of the nucleic acids provided herein which have a sequence not exactly previously identified; fragments having sequences with the indicated sequence identity to that portion not previously identified are provided in an embodiment herein.

In addition, as is more fully outlined below, Mkk3b proteins can be made that have a longer amino acid sequence than SEQ ID NO:2; for example, by the addition of epitope or purification tags, the addition of other fusion sequences (described below), or the elucidation of additional coding and non-coding sequences. As described below, the fusion of an Mkk3b peptide to a fluorescent protein, such as Blue Fluorescent Protein (BFP) or Green Fluorescent Protein (GFP), including those of *Aquorea* and *Renilla* species, is particularly preferred.

Mkk3b proteins may also be identified as encoded by Mkk3b nucleic acids which hybridize to the sequence depicted in SEQ ID NO:1 or the complement thereof, or fragments thereof or their complements, as outlined herein. Hybridization conditions are further described below.

In a preferred embodiment, when an Mkk3b protein is to be used to generate antibodies, an Mkk3b protein must share at least one epitope or determinant with the full length protein. By epitope or determinant herein is meant a portion of a protein which will generate and/or bind an antibody. Thus, in most instances, antibodies made to a smaller Mkk3b protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibodies to a Mkk3b protein are capable of reducing or eliminating the biological function of the Mkk3b proteins described herein, as is described below. That is, the addition of anti-Mkk3b antibodies (either polyclonal or preferably monoclonal) to Mkk3b proteins (or cells containing Mkk3b proteins) may reduce or eliminate their ability to modulate lymphocyte activation and/or other Mkk3b bioactivities described herein. Generally, at least a 25% decrease in activity is preferred, with at least about 50% being particularly preferred and about a 95-100% decrease being especially preferred.

The anti-Mkk3b antibodies of the invention bind to Mkk3b proteins. In a preferred embodiment, the antibodies specifically bind to Mkk3b proteins. By specifically bind herein is meant that the antibodies bind to the protein with a binding constant in the range of at least $10^{-4}$-$10^{-6}$ $M^{-1}$, with a preferred range being $10^{-7}$-$10^{-9}$ $M^{-1}$. Antibodies are further described below.

In the case of a Mkk3b nucleic acid, the overall sequence identity of the nucleic acid sequence is commensurate with amino acid sequence identity but takes into account the degeneracy in the genetic code and codon bias of different organisms. Accordingly, the nucleic acid sequence identity may be either lower or higher than that of the protein sequence. An Mkk3b nucleic acid of the present invention comprises a nucleic acid sequence that preferably has greater than about 75% identity to the nucleic acid sequence set forth in SEQ ID NO:1, more preferably greater than about 80%, particularly greater than about 85% and most preferably greater than 90%. In some embodiments the sequence identity will be as high as about 93 to 95 or 98%.

In a preferred embodiment, an Mkk3b nucleic acid encodes a Mkk3b protein. As will be appreciated by those in the art, due to the degeneracy of the genetic code, an extremely large number of nucleic acids may be made, all of which encode the Mkk3b proteins of the present invention. Thus, having identified a particular amino acid sequence, those skilled in the art could make any number of different nucleic acids, by simply modifying the sequence of one or more codons in a way which does not change the amino acid sequence of the Mkk3b protein.

In one embodiment, the Mkk3b nucleic acid is determined through hybridization studies. Thus, for example, nucleic acids which hybridize under high stringency conditions to the nucleic acid sequence shown in SEQ ID NO:1 the complement thereof, or fragments thereof or their complements, are considered Mkk3b nucleic acids. High stringency conditions are known in the art; see for example Maniatis et al., *Molecular Cloning: A Laboratory Manual*, 2d Edition, 1989, Cold Spring Harbor Press, Cold Spring Harbor, N.Y., and *Short Protocols in Molecular Biology*, ed. Ausubel, et al., John Wiley & Sons, NY, both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Acid Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see *Molecular Cloninq. A Laboratory Manual*, Sambrook et al., $3^{rd}$ edition, 2001, Cold Spring Harbor Press, Cold Spring Harbor, N.Y.; and Tijssen, supra.

The Mkk3b nucleic acids are substantially complementary to the recited nucleic acid sequence, such that hybridization of the Mkk3b nucleic acids and SEQ ID NO:1 occurs. As outlined below, this complementarity need not be perfect; there may be any number of base pair mismatches which will interfere with hybridization. However, if the number of mutations is so great that no hybridization can occur under even the least stringent of hybridization conditions, the sequence is not a complementary and is not considered an Mkk3b nucleic acid. Thus, by "substantially complementary" herein is meant that the nucleic acids are sufficiently complementary to the Mkk3b sequence set forth in SEQ ID NO:1 to hybridize under normal reaction conditions, particularly high stringency conditions, as outlined herein.

The Mkk3b proteins and Mkk3b nucleic acids of the present invention are preferably recombinant. As used herein and further defined below, nucleic acid may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the Figures also include the complement of the sequence. By the term recombinant nucleic acid herein is meant nucleic acid, originally formed in vitro, in general, by the manipulation of nucleic acid by endonucleases, in a form not normally found in nature. Thus an isolated Mkk3b nucleic acid, in a linear form, or an expression vector formed in vftro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a recombinant protein is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a Mkk3b protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides Mkk3b protein variants. These variants fall into one or more of three classes: substitutional, insertional or deletional variants. These variants ordinarily are prepared by site specific mutagenesis of nucleotides in the DNA encoding an Mkk3b protein, using cassette or PCR mutagenesis or other techniques well known in the art, to produce DNA encoding the variant, and thereafter expressing the DNA in recombinant cell culture as outlined above. However, variant Mkk3b protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the Mkk3b protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Mkk3b protein variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Mkk3b protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Mkk3b protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the Mkk3b proteins as needed. Alternatively, the variant may be designed such that the biological activity of the Mkk3b protein is altered. For example, glycosylation sites may be altered or removed.

In a preferred embodiment, Mkk3b variant proteins are provided which lack at least one Mkk3b protein activity. Accordingly, provided herein are Mkk3b variants comprising a mutation in the ATP binding pocket corresponding to the K93A mutation depicted in FIG. 1, and Mkk3b variants comprising mutations at regulatory sites corresponding to the S218A and T222A mutations depicted in FIG. 1.

In a preferred embodiment, the Mkk3b variant is unable to bind at least one Mkk3b binding partner. An Mkk3b binding partner may be identified by its ability to bind specifically to an Mkk3b protein comprising the amino acid sequence set forth in SEQ ID NO:2. the Mkk3b variant is unable to bind at least one Mkk3b binding partner of the group Btk, p38 and PP2C.

In another preferred embodiment, the Mkk3b variant lacks dual specificity kinase activity, particularly tyrosine and threonine kinase activity.

In another preferred embodiment, the Mkk3b variant is able to bind p38 but lacks the ability to phosphorylate and activate p38, preferably human p38, preferably on T180 and Y182.

In one aspect, such Mkk3b variant proteins exhibit dominant negative activity, i.e. they inhibit the activity of wild-type Mkk3b proteins. In one aspect, the dominant negative Mkk3b variant protein inhibits p38 phosphorylation. In one aspect, the dominant negative Mkk3b variant protein inhibits p38 activation. In one aspect, the dominant negative Mkk3b variant protein decreases basal lymphocyte activity. In one aspect, the dominant negative Mkk3b variant protein inhibits or decreases lymphocyte activation, for example in response to stimuli including but not limited to BCR, TCR, and CD40 activation.

In one embodiment, the dominant negative Mkk3b variant protein inhibits NFAT activity.

In one embodiment, the dominant negative Mkk3b variant protein inhibits the induction of surface markers which are normally expressed during lymphocyte activation, for example CD69, CD25 and CD80.

In a preferred embodiment, Mkk3b variant proteins are provided which have constitutive dual specificity kinase activity. Accordingly, provided herein are Mkk3b variants comprising activating mutations at regulatory sites corresponding to the S218E and T222E mutations depicted in FIG. 1.

In one aspect, such Mkk3b variants increase the phosphorylation of p38, preferably human p38, preferably on T180 and Y182. In one aspect, such Mkk3b variants increase p38 activity.

In one aspect, such Mkk3b variant proteins potentiate or increase lymphocyte activation, for example in response to stimuli including but not limited to BCR, TCR, and CD40 stimulation.

Covalent modifications of Mkk3b polypeptides are included within the scope of this invention. One type of covalent modification includes reacting targeted amino acid residues of an Mkk3b polypeptide with an organic derivatizing agent that is capable of reacting with selected side chains or the N- or C-terminal residues of an Mkk3b polypeptide. Derivatization with bifunctional agents is useful, for instance, for crosslinking Mkk3b to a water-insoluble support matrix or surface for use in the method for purifying anti-Mkk3b antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the -amino groups of lysine, arginine, and histidine side chains [T. E. Creighton, *Proteins: Structure and Molecular Properties*, W. H. Freeman & Co., San Francisco, pp. 79-86 (1983)], acetylation of the N-terminal amine, and amidation of any C-terminal carboxyl group.

Another type of covalent modification of the Mkk3b polypeptide included within the scope of this invention comprises altering the native glycosylation pattern of the polypeptide. Altering the native glycosylation pattern is intended for purposes herein to mean deleting one or more carbohydrate moieties found in native sequence Mkk3b polypeptide, and/or adding one or more glycosylation sites that are not present in the native sequence Mkk3b polypeptide.

Addition of glycosylation sites to Mkk3b polypeptides may be accomplished by altering the amino acid sequence thereof. The alteration may be made, for example, by the addition of, or substitution by, one or more serine or threonine residues to the native sequence Mkk3b polypeptide (for O-linked glycosylation sites). The Mkk3b amino acid sequence may optionally be altered through changes at the DNA level, particularly by mutating the DNA encoding the Mkk3b polypeptide at preselected bases such that codons are generated that will translate into the desired amino acids.

Another means of increasing the number of carbohydrate moieties on the Mkk3b polypeptide is by chemical or enzymatic coupling of glycosides to the polypeptide. Such methods are described in the art, e.g., in WO 87/05330 published 11 September 1987, and in Aplin and Wriston, *CRC Crit. Rev. Biochem., pp.* 259-306 (1981).

Removal of carbohydrate moieties present on the Mkk3b polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo-and exo-glycosidases as described by Thotakura et al., *Meth. Enzymol.,* 138:350 (1987).

Another type of covalent modification of Mkk3b comprises linking the Mkk3b polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Mkk3b polypeptides of the present invention may also be modified in a way to form chimeric molecules comprising an Mkk3b polypeptide fused to another, heterologous polypeptide or amino acid sequence. In one embodiment, such a chimeric molecule comprises a fusion of an Mkk3b polypeptide with a tag polypeptide which provides an epitope to which an anti-tag antibody can selectively bind. In a preferred embodiment, such a tag is the "flag tag" described below. The epitope tag is generally placed at the amino-or carboxyl-terminus of the Mkk3b polypeptide. The presence of such epitope-tagged forms of a Mkk3b polypeptide can be detected using an antibody against the tag polypeptide. Also, provision of the epitope tag enables the Mkk3b polypeptide to be readily purified by affinity purification using an anti-tag antibody or another type of affinity matrix that binds to the epitope tag. In an alternative embodiment, the chimeric molecule may comprise a fusion of an Mkk3b polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science* 255:192-194 (1992)]; tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

The Mkk3b protein may also be made as a fusion protein, using techniques well known in the art. Thus, for example, for the creation of monoclonal antibodies, if the desired epitope is small, the Mkk3b protein may be fused to a carrier protein to form an immunogen. Alternatively, the Mkk3b protein may be made as a fusion protein to increase expression, or for other reasons. For example, when the Mkk3b protein is an Mkk3b peptide, the nucleic acid encoding the peptide may be linked to other nucleic acid for expression purposes. Similarly, Mkk3b proteins of the invention can be linked to protein labels, such as green fluorescent protein (GFP), red fluorescent protein (RFP), blue fluorescent protein (BFP), yellow fluorescent protein (YFP), etc.

In an embodiment herein, Mkk3b protein family members and Mkk3b proteins from other organisms are cloned and expressed as outlined below. Thus, probe or degenerate polymerase chain reaction (PCR) primer sequences may be used to find other related Mkk3b proteins from humans or other organisms. As will be appreciated by those in the art, particularly useful probe and/or PCR primer sequences include the unique areas of the Mkk3b nucleic acid sequence. Particularly useful are those sequences which are unique to Mkk3b and are not found in other Mkk3 isoforms. Especially preferred are sequences encoding the first 29 amino acids of Mkk3b, or fragments thereof. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant Mkk3b nucleic acid can be further used as a probe to identify and isolate other Mkk3b nucleic acids. It can also be used as a precursor nucleic acid to make modified or variant Mkk3b nucleic acids and proteins.

Using the nucleic acids of the present invention which encode a Mkk3b protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Mkk3b protein. The term control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Mkk3b protein; for example, transcriptional and translational regulatory nucleic acid sequences from *Bacillus* are preferably used to express the Mkk3b protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Mkk3b proteins of the present invention are produced by culturing a host cell transformed with an expression vector containing Mkk3b nucleic acid encoding an Mkk3b protein under the appropriate conditions to induce or cause expression of the Mkk3b protein. The conditions appropriate for Mkk3b protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, *Neurospora*, BHK, CHO, COS, and HeLa cells, fibroblasts, Schwanoma cell lines, immortalized mammalian myeloid and lymphoid cell lines.

In a preferred embodiment, the Mkk3b proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for Mkk3b protein into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Mkk3b proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Mkk3b into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the Mkk3b protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris*, and *Streptococcus lividans*, among others.

The bacterial expression vectors are transformed into bacterial host cells using techniques well known in the art, such as calcium chloride treatment, electroporation, and others.

In one embodiment, Mkk3b proteins are produced in insect cells. Expression vectors for the transformation of insect cells, and in particular, baculovirus-based expression vectors, are well known in the art.

In a preferred embodiment, Mkk3b protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastons, Schizosaccharomyces pombe*, and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

In one embodiment, the Mkk3b nucleic acids, proteins and antibodies of the invention are labeled. By labeled herein is meant that a compound has at least one element, isotope or chemical compound attached to enable the detection of the compound. In general, labels fall into four classes: a) isotopic labels, which may be radioactive or heavy isotopes; b) immune labels, which may be antibodies or antigens; c) magnetic, electrical, thermal; and d) colored or fluorescent dyes. The labels may be incorporated into the compound at any position. Examples of such labels include: peroxidase; alkaline phosphatase; biotin; urease; beta-galactosidase; BSA/KLH; gold particles; quantum dots; redox indicators; pH indicators; b-lactamase; luciferase; TSA; SPA; chemiluminescence; sonoluminescence; fluorophores; phosphors; and, fluorescent metal ion sensors. Preferred labels include luminescent labels. In a preferred embodiment, the Mkk3b nucleic acid, protein or antibody is directly labeled, that is, the Mkk3b nucleic acid, protein or antibody comprises a label. In an alternate embodiment, the Mkk3b nucleic acid, protein or antibody is indirectly labeled; that is, a labeling binding ligand (LBL) that will bind to the Mkk3b nucleic acid, protein or antibody is used. Suitable labels include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, FITC, PE, cy3, cy5 and others described in the 6th Edition of the Molecular Probes Handbook by Richard P. Haugland, hereby expressly incorporated by reference.

In a preferred embodiment, the Mkk3b protein is purified or isolated after expression. Mkk3b proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Mkk3b protein may be purified using a standard anti-Mkk3b antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the Mkk3b protein. In some instances no purification will be necessary.

Once expressed and purified if necessary, the Mkk3b proteins and nucleic acids are useful in a number of applications.

The nucleotide sequences (or their complement) encoding Mkk3b proteins have various applications in the art of molecular biology, including uses as hybridization probes, in chromosome and gene mapping and in the generation of anti-sense RNA and DNA. Mkk3b nucleic acids will also be useful for the preparation of Mkk3b proteins by the recombinant techniques described herein.

The full-length native sequence Mkk3b protein gene, or portions thereof, may be used as hybridization probes for a cDNA library to isolate other genes (for instance, those encoding naturally-occurring variants of Mkk3b protein or Mkk3b protein from other species) which have a desired sequence identity to the Mkk3b protein coding sequence. Optionally, the length of the probes will be about 20 to about 50 bases. Preferably the probe sequence will be unique to Mkk3b and not found in other known Mkk3 isoforms. The hybridization probes may be derived from the nucleotide sequences herein or from genomic sequences including promoters, enhancer elements and introns of native sequences as provided herein. By way of example, a screening method will comprise isolating the coding region of the Mkk3b protein gene using the known DNA sequence to synthesize a selected probe of about 40 bases. Hybridization probes may be labeled by a variety of labels, including fluorophores, radionucleotides such as $^{32}P$ or $^{35}S$, or enzymatic labels such as alkaline phosphatase or horse radish peroxidase (HRP) coupled to the probe in a variety of ways, including, but not limited to, avidin/biotin coupling systems and chemical linkers. Labeled probes having a sequence sufficiently complementary to that of the Mkk3b protein gene of the present invention can be used to screen libraries of human cDNA, genomic DNA or mRNA to determine which members of such libraries the probe hybridizes.

Nucleotide sequences encoding an Mkk3b protein can also be used to construct hybridization probes for mapping the gene which encodes that Mkk3b protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode Mkk3b protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding an Mkk3b protein can be used to clone genomic DNA encoding an Mkk3b protein in accordance with established techniques and the genomic sequences used to generate transgenic animals that contain cells which express the desired DNA. Methods for generating transgenic animals, particularly animals such as mice or rats, have become conventional in the art and are described, for example, in U.S. Pat. Nos. 4,736,866 and 4,870,009, each of which is expressly incorporated herein by reference. Typically, particular cells would be targeted for expression of the transgenic Mkk3b protein with tissue-specific enhancers. Transgenic animals that include a copy of a transgene encoding a Mkk3b protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the Mkk3b protein can be used to construct a Mkk3b protein "knock out" animal which has a defective or altered gene encoding a Mkk3b protein as a result of homologous recombination between the endogenous gene encoding a Mkk3b protein and altered genomic DNA encoding a Mkk3b protein introduced into an embryonic cell of the animal. For example, cDNA encoding a n Mkk3b protein can be used to clone genomic DNA encoding an Mkk3b protein in accordance with established techniques. A portion of the genomic DNA encoding an Mkk3b protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Mkk3b protein.

It is understood that the models described herein can be varied. For example, "knock-in" models can be formed, or the models can be cell-based rather than animal models.

Nucleic acid encoding the Mkk3b polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et. al., *J. Biol. Chem.* 262, 4429-4432 (1987); and Wagner et a., *Proc. Natl. Acad. Sci. USA* 87, 3410-3414 (1990). For review of gene marking and gene therapy protocols see Anderson et. al., *Science* 256, 808-813 (1992).

In a preferred embodiment, the Mkk3b proteins, nucleic acids, variants, modified proteins, cells and/or transgenics containing the said nucleic acids or proteins are used in screening assays. Identification of the Mkk3b proteins provided herein permits the design of drug screening assays for compounds that modulate Mkk3b protein binding, Mkk3b protein activity, lymphocyte activation, p38 activity, and CD80 expression.

The assays described herein preferably utilize the human Mkk3b protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, variant or derivative Mkk3b proteins may be used, including Mkk3b variants which lack dual specificity kinase activity, or Mkk3b variants with constitutive kinase activity.

A variety of other reagents may be included in the assays. These include reagents like salts, neutral proteins, e.g. albumin, detergents, etc. These may be included for example to facilitate optimal protein-protein binding and/or reduce non-specific or background interactions. Also reagents that otherwise improve the efficiency of the assay, such as protease inhibitors, nuclease inhibitors, anti-microbial agents, etc., may be used.

In a preferred embodiment, the methods comprise combining an Mkk3b protein and a candidate bioactive agent, and determining the binding of the candidate agent to the Mkk3b protein. In other embodiments, further discussed below, binding interference or modulation of bioactivity is determined.

The term "candidate bioactive agent" or "exogeneous compound" or "candidate agent" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind Mkk3b protein (such as Btk, p38 or PP2C), may be used.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the presents methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus amino acid, or peptide residue, as used herein means both naturally occurring and synthetic amino acids. For example, homo-phenylalanine, citrulline and norleucine are considered amino acids for the purposes of the invention. Amino acid also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred, and 12 and 18 amino acids being most preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or oligonucleotide or grammatical equivalents herein means at least two nucleotides covalently linked together. A nucleic acid of the present invention will generally contain phosphodiester bonds, although in some cases, as outlined herein, particularly with respect to antisense nucleic acids or probes, nucleic acid analogs are included that may have alternate backbones, comprising, for example, phosphoramide (Beaucage, et al., *Tetrahedron*, 49(10):1925 (1993) and references therein; Letsinger, *J. Org. Chem.*, 35:3800 (1970); Sprinzl, et al., *Eur. J. Biochem.*, 81:579 (1977); Letsinger, et al., Nucl. Acids Res. 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114: 1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowski, et. al., Angew. Chem. Intl. Ed. English, 30:423 (1991); Letsinger, et a., J. Am. Chem. Soc., 110:4470 (1988); Letsinger, et. al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., Chem. Soc. Rev., (1995) pp.169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties or small molecule chemical compositions, a wide variety of which are available in the literature.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed. For example see U.S. Pat. No. 6,153,380, expressly incorporated herein by reference.

In some embodiments of the invention, candidate agents are contacted to cells and/or samples. By "contacting" is meant exposing to, combining with, introducing to, introducing into, placing in, or other grammatical equivalents. Importantly, by "contacting" a cell or sample with candidate agent, interaction or reaction of the candidate agent with a component of the cell or sample it is brought into contact with is facilitated.

In some embodiments of the invention, portions of Mkk3b proteins are utilized; in a preferred embodiment, portions having Mkk3b activity as described herein are used. In a preferred embodiment, portions comprising a kinase domain are used. In a preferred embodiment, assays which involve screening for a change in Mkk3b kinase activity make use of a portion of Mkk3b that consists essentially of the kinase domain. In other preferred embodiments, full length Mkk3b protein is used. In another preferred embodiment, portions comprising the amino acid sequence set forth by the first 29 amino acids in SEQ ID NO:2 are used. The assays described herein may utilize either isolated Mkk3b proteins or cells comprising the Mkk3b proteins. In some preferred embodiments, cell-free samples comprising Mkk3b protein are used.

In one aspect, binding of Mkk3b to Mkk3b binding partner, for example Btk, PP2C or p38, is determined. In one embodiment, the methods involve determining binding by performing a coimmunoprecipitation assay from lysates collected from cells expressing Mkk3b and Mkk3b binding partner. Methods for performing a coimmunoprecipitation assay are well known in the art, for example see Current Protocols in Protein Science, Coligan et al., supra, Chapter 19 "Identification of Protein Interactions", expressly incorporated herein by reference.

Generally, in a preferred embodiment of the methods herein, for example for binding assays, the Mkk3b protein or the candidate agent Is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the Mkk3b protein is bound to the support, and a candidate bioactive agent is added to the assay. Alternatively, the candidate agent is bound to the support and the Mkk3b protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the Mkk3b protein may be done in a number of ways. In a preferred embodiment, the candidate bioactive agent is labelled, and binding determined directly. For example, this may be done by attaching all or a portion of the Mkk3b protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, as described above.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. Mkk3b protein), such as an antibody, peptide, binding partner, ligand, etc. In a preferred embodiment, the competitor Btk, p38 or PP2C. Under certain circumstances, there may be competitive binding as between the bioactive agent and the binding moiety, with the binding moiety displacing the bioactive agent. This assay can be used to determine candidate agents which interfere with binding between Mkk3b proteins and Btk, p38 or PP2C. "Interference of binding" as used herein means that native binding of the Mkk3b protein differs in the presence of the candidate agent. The binding can be eliminated or can be with a reduced affinity. Therefore, in one embodiment, interference is caused by, for example, a conformational change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the Mkk3b protein and thus is capable of binding to, and potentially modulating, the activity of the Mkk3b protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the Mkk3b protein with a higher affinity. Thus, if the candidate bioactive agent is labeled, the presence of the label on the support, coupled with a lack of competitor binding, may indicate that the candidate agent is capable of binding to the Mkk3b protein.

In a preferred embodiment, the methods comprise differential screening to identity bioactive agents that are capable of modulating the activity of the Mkk3b proteins. Such assays can be done with the Mkk3b protein or cells comprising Mkk3b protein. Mkk3b protein may be recombinant Mkk3b protein produced and collected as described herein, or may be a cell lysate from a cell comprising an Mkk3b protein or a recombinant Mkk3b protein. In one embodiment, the methods comprise combining an Mkk3b protein and a competitor in a first sample. A second sample comprises a candidate bioactive agent, an Mkk3b protein and a competitor. The binding of the competitor is determined for both samples, and a change or difference in binding between the two samples indicates the presence of an agent capable of binding to the Mkk3b protein and modulating its activity. That is, if the binding of the competitor is different in the second sample relative to the first sample, the agent is capable of binding to the Mkk3b protein and modulating its activity.

Alternatively, a preferred embodiment utilizes differential screening to identify drug candidates that bind to the native Mkk3b protein, but cannot bind to modified Mkk3b proteins. The structure of the Mkk3b protein may be modeled, and used in rational drug design to synthesize agents that interact with that site. Drug candidates that affect Mkk3b bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of an Mkk3b protein may also be done. In a preferred embodiment, methods for screening for a bioactive agent capable of modulating the activity of an Mkk3b protein comprise the steps of adding a candidate bioactive agent to a sample of an Mkk3b protein (or a cell comprising a n Mkk3b protein) and determining an alteration in the biological activity of the Mkk3b protein. A sample of an Mkk3b protein may be obtained by recombinantly producing and collecting Mkk3b protein, as described herein, or by obtaining a cell lysate from a cell comprising a Mkk3b protein or a recombinant Mkk3b protein by means known in the art. "Modulating the activity of an Mkk3b protein" includes an increase in activity, a decrease in activity, or a change in the type or kind of activity present. Thus, in this embodiment, the candidate agent may bind to a Mkk3b protein (although this may not be necessary), and should alter its biological or biochemical activity as defined herein. The methods include both in vitro screening methods, as are generally outlined above, and in vivo screening of cells for alterations in the presence, cellular distribution, subcellular distribution, activity or amount of Mkk3b protein. In vitro assays may be performed using cell lysates following in vivo manipulations involved in screens.

By "Mkk3b protein activity" or grammatical equivalents herein is meant at least one of the Mkk3b protein's biological activities, as described above.

In a preferred embodiment, the activity of the Mkk3b protein is decreased by the agent; in another preferred embodiment, the activity of the Mkk3b protein is increased by the agent. Thus, bioactive agents that are antagonists are preferred in some embodiments, and bioactive agents that are agonists are preferred in other embodiments. Bioactive agents that are antagonists of Mkk3b activity find use as immunosuppressants.

In a preferred embodiment, the invention provides methods of screening for bioactive agents capable of modulating the activity of an Mkk3b protein. The methods comprise adding a candidate bioactive agent, as defined above, to a cell comprising an Mkk3b protein. The cell contains a recombinant nucleic acid that encodes an Mkk3b protein that is expressed in the cell. In a preferred embodiment, a library of candidate agents are tested on a plurality of cells. Preferred cell types include Ig(+) B cell lines, including the CL-01, LA350, BJAB and CA46 cell lines. T cell lines, including Jurkat cells, may also be used.

Primary B and T cells are also preferred. Primary B cells are preferably obtained by negative selection from peripheral blood monocytes as is known in the art, for example by using antibodies against CD2, CD3, CD7, CD14, CD16, and CD56. Purity of the cell population obtained may be confirmed by analysis of CD19 expression, for example by FACS. Primary B cell purity greater than 90% can be routinely obtained by such selection methods.

Some preferred embodiments involve contacting the candidate bioactive agent to a lymphocyte, and determining lymphocyte activation in the presence of said candidate agent. In a preferred embodiment, lymphocyte activation in the presence and absence of candidate agent is determined.

In a preferred embodiment, an agent that normally induces lymphocyte activation is used. Lymphocyte activation is measured in the presence, and optionally, the absence of candidate agent following contact with the agent that normally induces lymphocyte activation. Preferred activation agent for use with B lymphocytes are anti-IgM antibody and CD40L. A preferred activation agent for use with T lymphocytes is C305, an anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

It will be understood that while agents that normally induce lymphocyte activation (i.e., activation agents) are used, the screening method is designed to identify agents that are capable of modulating lymphocyte activation. Accordingly, the presence of a bioactive agent that is capable of inhibiting lymphocyte activation may preclude activation of the lymphocyte by the activation agent. Such agents are nevertheless referred to herein as activation agents, and the step of contacting the cells with such an activation agent is frequently referred to herein as "inducing lymphocyte activation", even though a candidate bioactive agent may inhibit such activation by the agent. This nomenclature applies to the methods that follow as well. Bioactive agents that inhibit lymphocyte activation in these assays find use as immunosuppressants.

In some preferred embodiments, screening for a bioactive agent capable of modulating Mkk3b activity involves expressing Mkk3b nucleic acid in a lymphocyte or APC, contacting the expressing cell with a candidate agent, and determining the level of expression of a surface marker which is normally associated with lymphocyte activation in the presence of candidate agent. In a preferred embodiment, the level of surface marker expression is determined in the presence and absence of candidate agent. In a preferred embodiment, the surface marker is selected from the group consisting of CD69, CD80 and CD25.

In a preferred embodiment, the method involves screening for an agent that can enhance expression of a BCR-induced activation marker or a CD40-induced costimulatory molecule. In a preferred embodiment, B cells are used and the method additionally involves stimulating CD40 or BCR in B cells prior to contacting B cells with candidate bioactive agent. In another preferred embodiment, B cells are contacted with candidate agent prior to BCR or CD40 stimulation. Preferably, BCR stimulation involves the use of anti-IgM antibody, while CD40 stimulation preferably involves the use of CD40L. Preferably, at least one of CD80, CD25, and CD69 expression is determined following CD40 stimulation or BCR stimulation.

In a preferred embodiment, antigen presenting cells (APCs) are used and the method additionally involves stimulating CD40 in APCs prior to contacting APCs with candidate bioactive agent. In another preferred embodiment, APCs are contacted with candidate agent prior to CD40 stimulation. Preferably, CD40 stimulation involves the use of CD40L. Preferably, CD80 or CD25 expression is determined following CD40 stimulation.

In a preferred embodiment, determining the expression of a surface marker is done using an antibody that specifically binds to the surface marker. In a preferred embodiment, detecting surface marker expression is done by sorting cells by FACS on the basis of surface marker expression as determined using marker-specific labeled antibodies, as is well known in the art.

In a preferred embodiment, screening for a bioactive agent capable of modulating Mkk3b activity involves expressing Mkk3b nucleic acid in a lymphocyte, contacting the expressing cell with a candidate bioactive agent, and determining the level of activity of a promoter which activity normally correlates with lymphocyte activation, in the presence of candidate agent. In a preferred embodiment, the level of promoter activity is determined in the presence and absence of candidate agent. In a preferred embodiment the promoter is an NFAT-responsive promoter, e.g., IL-2 promoter, which is capable of reporting NFAT activity.

In a preferred embodiment, the method involves screening for an agent capable of enhancing TCR-induced promoter activation. In a preferred embodiment, T cells are used and the method additionally involves stimulating TCR in T cells prior to contacting T cells with candidate bioactive agent. In another preferred embodiment, T cells are contacted with candidate agent prior to TCR stimulation. Preferably, TCR stimulation involves the use of anti-CD3 antibody.

In a preferred embodiment, the method involves screening for an agent capable of enhancing BCR-induced promoter activation. In one embodiment of the method, B cells are used and the method additionally involves stimulating BCR in B cells prior to contacting B cells with candidate bioactive agent. In another preferred embodiment, B cells are contacted with candidate agent prior to BCR stimulation. Preferably, BCR stimulation involves the use of anti-IgM antibody. In a preferred embodiment, the CD40 complex on B cells is stimulated and the effect of candidate agent on the induction of promoter activity is determined.

In a preferred embodiment, screening for a bioactive agent capable of modulating Mkk3b activity involves determining p38 activity. In one aspect, the method comprises expressing Mkk3b nucleic acid in a lymphocyte or APC, contacting the expressing cell with a candidate bioactive agent, and determining the activity of p38. In a preferred embodiment, the method involves determining the phosphorylation of p38, preferably the threonine and/or tyrosine phosphorylation of p38, preferably the phosphorylation of T180 and Y182 of human p38. In a preferred embodiment, anti-phospho-p38 antibody which specifically recognizes phosphorlayted p38 is used to detect phosphorylated p38. In a preferred embodiment, determining p38 phosphorylation involves sorting cells by FACS on the basis of the presence of phosphorylated p38.

In another preferred embodiment, determining the activity of p38 involves performing a kinase assay using a substrate which is capable of being phosphorylated by p38. In one embodiment, a kinase assay is done using ATF2 as such a p38 substrate.

In one embodiment, T cells are used and the method additionally involves stimulating TCR in T cells prior to contacting T cells with candidate bioactive agent. In another preferred embodiment, T cells are contacted with candidate agent prior to TCR stimulation. Preferably, TCR stimulation involves the use of anti-CD3 antibody.

In one embodiment, B cells are used and the method additionally involves stimulating CD40 or BCR in B cells prior to contacting B cells with candidate bioactive agent. In another preferred embodiment, B cells are contacted with candidate agent prior to BCR or CD40 stimulation. Preferably, BCR stimulation involves the use of anti-IgM antibody, while CD40 stimulation preferably involves the use of CD40L.

In one embodiment, antigen presenting cells (APCs) are used and the method additionally involves stimulating CD40 in APCs prior to contacting APCs with candidate bioactive agent. In another preferred embodiment, APCs are contacted with candidate agent prior to CD40 stimulation. Preferably, CD40 stimulation involves the use of CD40L.

In one embodiment, the methods comprise using an in vitro kinase assay to determine p38 activity. Such kinase assays are well known in the art, for example see Derijard et. al., Science 267:682-685, 1995; Han et. al., FEBS Letters 403:19-22,1997; Davis et. al., U.S. Pat. No. 5,736,381; Davis et. al., U.S. Pat. No. 5,804,427; Davis et. al. WO 96/36642; all of which are expressly incorporated herein by reference. Methods for performing kinase assays in general are well known in the art, for example see *Current Protocols in Protein Science*, supra, Chapter 13 "Post-translational modification: phosphorylation and phosphatases", expressly incorporated herein by reference.

In a preferred embodiment, the method comprises using anti-phospho-p38 antibody to determine p38 phosphorylation. Such phospho-p38 antibodies are known, see for example see Promega Anti-Active® p38 polyclonal rabbit antibody, catalog number v1211.

Screening for agents that modulate lymphocyte activation may also be done. In one aspect, the method involves screening for an agent capable of binding to Mkk3b protein using assays provided herein. In one aspect, the method involves screening for an agent capable of modulating Mkk3b binding using assays provided herein. In one aspect, the method involves screening for an agent that will modulate Mkk3b activity using assays provided herein.

In a preferred embodiment, the method comprises determining Mkk3b phosphorylation using anti phospho-Mkk3b antibody. Such antibodies are known, see for example Cell Signaling Technology, Beverley Mass., catalog #9231.

In some embodiments, the methods involve determining lymphocyte activation. As will be appreciated, lymphocyte activation can be determined in a number of ways, and methods for the determination of T lymphocyte and B lymphocyte are generally known, for example see *Current Protocols in Immunology*, John Wiley and Sons Publ., J. E. Coligan et. al. editors, ISBN 047 1306606, published April 1993, edited October 2001, Chapter 3 "in Vitro Assays for Mouse Lymphocyte Activation", expressly incorporated herein by reference. It will be appreciated that mechanisms of lymphocyte activation and methods for determining activation are known (see for example Kay, Immunol. Invest. 17:679-705,1988; Lukacs et. al., Chem. Immunol. 72:102-120, 1999; Metcalf et. al., Physiol. Rev. 77:1033-1079, 1997; Hematol. Oncol. Clin. North Am. 4:1-26,1990; Brass et. al., Adv. Exp. Med. Biol., 344:17-36, 1993; Brass et. al., Thromb. Haemost., 70:217-223, 1993; *Cellular and Molecular Immunology*, Abbas et. al., W. B. Saunders, ISBN 0-7216-3032-4, Chapters 7, 9, 12, and 14), expressly incorporated herein by reference.

In one embodiment, indicators of lymphocyte activation are used. There are a number of parameters that may be evaluated or assayed to determine lymphocyte activation, including, but not limited to, immunoglobulin heavy chain gene promoter activity, NFAT activity, Ig secretion, IgG and IgM production, lymphocyte proliferation, expression cell surface markers correlated with lymphocyte activation, cytokine production, release of calcium from intracellular stores, amount of SYK protein, level of SYK protein ubiquitination, SYK protein tyrosine kinase activity, ubiquitin specific protease activity directed to ubiquitin-conjugated SYK protein, Mkk3b activity, Mkk3b phosphorylation, p38 phosphorylation and p38 activity. These parameters may be assayed and used as indicators to evaluate the effect of candidate drug agents on lymphocyte activation. In this manner, rapid, accurate screening of candidate agents may be performed to identify agents that modulate lymphocyte activation.

In one aspect, the assays include exposing lymphocytes comprising recombinant Mkk3b protein to a T cell or B cell activation agent that will induce T cell or B cell activation in the absence of candidate agent. Alternatively, the cells may be exposed to conditions that normally result in T cell and B cell activation. The effect of the candidate agent on T cell and B cell activation is then evaluated. Preferred activation agents include anti-IgM antibody, anti-CD3 antibody, and CD40L.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. The cells may be in any cell phase, either synchronously or not, including M, G1, S, and G2. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colonrectal, leukemia, brain, etc. More preferable cell types include Jurkat cells and the Ig(+) and IgM secreting B cell lines CL-01, LA350 and CA46.

Preferred cell surface markers in the present invention exhibit low background expression in the absence of lymphocyte activation. Especially preferred cell surface markers include CD69, CD80, and CD25.

Agents that recognize such surface molecules (e.g. antibodies) can be used as an affinity ligand, and attached to a solid support such as a bead, a surface, etc., and used to pull out cells that are undergoing T cell and B cell activation. Similarly, these agents can be coupled to a fluorescent dye such as PerCP, and then used as the basis of a fluorescence-activated cell sorting (FACS) separation. Methods for sorting cells on the basis of immunofluorescence are well known, for example see *Current Protocols in Immunology*, supra, Chapter 5 "Immunofluorescence and Cell Sorting", expressly incorporated herein by reference.

FACS analysis can be used in conjunction with antibodies recognizing lymphocyte surface markers that are correlated with lymphocyte activation. FACS analysis is used to determine expression of these markers in unstimulated and stimulated lymphocytes which may additionally or alternatively be exposed to cytokines.

Immunoglobulin heavy chain gene promoter activity and NFAT activity can be measured using lymphocyte clones comprising an immunoglobulin heavy chain gene promoter or an NFAT-driven promoter (such as the IL-2 promoter) operably fused to a reporter gene. For example, a surface Ig(+), IgM secreting B cell line such as the CL-01, CA46, or LA350 cell line is transfected with a construct comprising GFP/2a/TK fusion under the control of an immunoglobulin heavy chain promoter, Eμ and 3'α enhancer elements. Stable transfectants (referred to herein as immunoglobulin heavy chain reporter cell lines) are selected and maintained in gancyclovir. Preferred immunoglobulin heavy chain reporter cell lines for use in the present invention exhibit low background GFP expression and strong basal activity and/or inducible activity in the presence of positive control. Such cell lines can be generated with the use of retroviral constructs.

Immunoglobulin heavy chain reporter cell lines are transfected with Mkk3b nucleic acids which are expressed in the cell lines. A FACS machine may be used to determine reporter gene (GFP) expression in Mkk3b-transfected immunoglobulin heavy chain cell lines, comparing reporter gene expression in cells exposed to anti-Ig and not exposed to anti-Ig. In one embodiment, Mkk3b protein affects basal reporter gene expression. In a preferred embodiment, reporter gene expression is determined in the presence and absence of candidate bioactive agents in immunoglobulin heavy chain cell lines stimulated and not stimulated with anti-Ig. In another preferred embodiment, reporter gene expression is determined in the presence and absence of candidate bioactive agents as they are tested for their ability to modulate the effect of Mkk3b protein on basal reporter gene expression, i.e. absent BCR, TCR, or CD40 stimulation.

Similarly, NFAT reporter cell lines comprising an NFAT activity reporter operably linked to a reporter gene may be made.

Release of calcium from intracellular calcium stores may be assayed using membrane permeant vital calcium sensing fluorescent dyes, as are well known in the art. For example, see Calcium Green™, Calcium Orange™, from Molecular Probes, Eugene, Oreg., catalog numbers C-3010, C-3013, for example.

A preferred embodiment utilizes a cell proliferation assay. By "proliferation assay" herein is meant an assay that allows the determination that a cell population is either proliferating, e.g., replicating, or not replicating. For example, see U.S. application Ser. No. 09/293,670, filed 16 Apr. 1999, incorporated herein in its entirety by reference.

In a preferred embodiment, the proliferation assay is a dye inclusion assay. A dye inclusion assay relies on dilution effects to distinguish between cell phases. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

The rate of loss of fluorescence is indicative of the rate of proliferation. An increase in proliferation rate above that of unstimulated cells is indicative of B cell activation.

Generally, the introduction of the inclusion dye may be done in one of two ways. Either the dye cannot passively enter the cells (e.g. it is charged), and the cells must be treated to take up the dye; for example through the use of a electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook; chapter 15 in particular.

In general, inclusion dyes are provided to the cells at a concentration ranging from about 100 ng/ml to about 5 µg/ml, with from about 500 ng/ml to about 1 µg/ml being preferred. A wash step may or may not be used. In a preferred embodiment, a candidate bioactive agent is combined with the cells as described herein. The cells and the inclusion dye are incubated for some period of time, to allow cell division and thus dye dilution.

In one aspect, the invention provides methods for screening for bioactive agents capable of modulating p38 activation. In a preferred embodiment, the methods comprise expressing Mkk3b nucleic acid in a lymphocyte or antigen presenting cell (APC), which cell also expresses the surface antigen CD40, contacting the cell with a candidate bioactive agent, stimulating CD40 in the cell, and determining the expression of CD80 in the cell. In a preferred embodiment, determining CD80 expression involves the use of anti-CD80 antibody and sorting cells by FACS on the basis of CD80 expression. Preferably CD40 is stimulated using CD40L.

In one embodiment, B cells are used and the method involves stimulating CD40 in B cells prior to contacting B cells with candidate bioactive agent. In another preferred embodiment, B cells are contacted with candidate agent prior to CD40 stimulation.

In one embodiment, antigen presenting cells (APCs) are used and the method involves stimulating CD40 in APCs prior to contacting APCs with candidate bioactive agent. In another preferred embodiment, APCs are contacted with candidate agent prior to CD40 stimulation.

Without being bound by theory, it is recognized herein that Mkk3b proteins are involved in the regulation of signal transduction in lymphocytes. Particularly, Mkk3b proteins are recognized herein as being critical regulators of B cell and T cell activation. As discussed above, the activation of specific signaling pathways in lymphocytes determines the quality, magnitude, and duration of immune responses. In transplantation, acute and chronic inflammatory diseases, and autoimmunity, it is these pathways that are responsible for the induction, maintenance and exacerbation of undesirable lymphocyte responses.

In a preferred embodiment, without being bound by theory, the present invention provides Mkk3b proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant.

In a preferred embodiment, without being bound by theory, the present invention provides Mkk3b proteins and nucleic acids, as well as agents that bind to them and/or modulate their activity, including and preferably small molecule chemical compositions as discussed herein, which are useful in the treatment of physiological states associated with the presentation of some or all symptoms characteristic of acute inflammatory disease, chronic inflammatory disease, autoimmune disease, or response to transplantation.

In a preferred embodiment, without being bound by theory, the present invention provides Mkk3b proteins and nucleic acids, as well as agents that bind to them and/or modulate their activity, including and preferably small molecule chemical compositions as discussed herein, which are useful as prophylactics directed to acute inflammatory disease, chronic inflammatory disease, autoimmune disease, and response to transplantation.

In a preferred embodiment, without being bound by theory, the present invention provides Mkk3b proteins and nucleic acids, as well as agents that bind to them and/or modulate their activity, including and preferably small molecule chemical compositions as discussed herein, which are useful as prophylactics directed to physiological states associated with the presentation of some or all symptoms characteristic of acute inflammatory disease, chronic inflammatory disease, autoimmune disease, or response to transplantation.

Without being bound by theory, it is recognized herein that Mkk3b proteins play an important role in the regulation of lymphocyte proliferation. Accordingly, it is recognized herein that dysfunction or dysregulation of Mkk3b proteins and nucleic acids, as well as Mkk3b signaling pathways and molecules associated with Mkk3b proteins and nucleic acids, can lead to deregulated cell proliferation, the hallmark of cancer.

Without being bound by theory, the present invention provides Mkk3b proteins and nucleic acids, as well as agents that bind to them and/or modulate their activity, including and preferably small molecule chemical compositions as discussed herein, which are useful in the treatment of T cell and B cell cancers.

Without being bound by theory, the present invention provides Mkk3b proteins and nucleic acids, as well as agents binding to them or modulating their activity, including and preferably small molecule chemical compositions as discussed herein, which are useful in the treatment of disorders involving T cell and B cell survival and programmed cell death including cancer.

The proteins and nucleic acids provided herein can also be used for screening purposes wherein the protein-protein interactions of the Mkk3b proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463. a preferred system is described in Ser. Nos. 09/050,863, filed Mar. 30, 1998 and 09/359,081 filed Jul. 22, 1999, entitled "Mammalian Protein Interaction Cloning System". For use in conjunction with these systems, particularly useful shuttle vectors are described in U.S. Pat. Nos. 6,280, 937 and 6,391,582, both expressly incorporated herein by reference.

In general, two nucleic acids are transformed into a cell, where one is a "bait" such as the gene encoding an Mkk3b protein or a portion thereof, and the other encodes a test candidate. Only if the two expression products bind to one another will an indicator, such as a fluorescent protein, be expressed. Expression of the indicator indicates when a test candidate binds to the Mkk3b protein, and identifies the candidate as being part of a T cell or B cell Mkk3b signaling pathway. A test candidate so identified may then be used as bait to identify binding proteins that are also identified as being part of a T cell or B cell Mkk3b signaling pathway. Additionally, Mkk3b proteins may be used to identify new baits, or agents that bind to Mkk3b proteins. Additionally, the two-hybrid system can be used wherein a test candidate is added in addition to the bait and the Mkk3b protein encoding nucleic acids to determine agents which interfere with the binding of bait, such as Btk or p38, to the Mkk3b protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can effect protein-protein interactions, particularly those involved in cancer.

Assays involving binding such as the two-hybrid system may take into account non-specific binding proteins (NSB).

Expression in various cell types, and assays for Mkk3b activity are described above. The activity assays can be performed to confirm the activity of Mkk3b proteins which have already been identified by their sequence identity/similarity to Mkk3b, as well as to further confirm the activity of lead compounds identified as modulators of Mkk3b activity.

The components provided herein for the assays provided herein may also be combined to form kits. The kits can be based on the use of the protein and/or the nucleic acid encoding the Mkk3b proteins. In one embodiment, other components are provided in the kit. Such components include one or more of packaging, instructions, antibodies, and labels. Additional assays such as those used in diagnostics are further described below.

In this way, bioactive agents are identified. Compounds with pharmacological activity are able to enhance or interfere with the activity of the Mkk3b protein. The compounds having the desired pharmacological activity may be administered in a physiologically acceptable carrier to a host, as further described below.

The present discovery relating to the role of Mkk3b proteins in lymphocytes thus provides methods for inducing or preventing lymphocyte activation. In a preferred embodiment, the Mkk3b proteins, and particularly Mkk3b protein fragments, are useful in the study or treatment of conditions which involve dysfunction or dysregulation of Mkk3b protein activity, i.e. to diagnose, treat or prevent Mkk3b-mediated disorders. Thus, "Mkk3b-mediated disorders" or "disease states" or "physiological states associated with Mkk3b dysfunction or dysregulation" include conditions involving insufficient, excessive, and inappropriate lymphocyte activation.

In addition, the present discovery relating to the role of Mkk3b in APCs provides methods for inducing or preventing the costimulation of T lymphocyte activation by APCs.

Thus, in one embodiment, methods for regulating lymphocyte activation in cells or organisms are provided. In one embodiment, the methods comprise administering to a cell or individual in need thereof, an Mkk3b protein in a therapeutic amount. Alternatively, an anti-Mkk3b antibody that reduces or eliminates the biological activity of the endogenous Mkk3b protein is administered. Alternatively and preferably an Mkk3b dominant negative protein variant is administered. In another preferred embodiment, a bioactive agent as identified by the methods provided herein is administered. In a further preferred embodiment, such an agent is a small molecule chemical composition which inhibits Mkk3b activity. Alternatively, the methods comprise administering to a cell or individual a recombinant nucleic acid encoding an Mkk3b protein. In one embodiment, nucleic acid encoding a Mkk3b dominant negative variant protein is administered. In another embodiment, an Mkk3b antisense nucleic acid is administered.

In one embodiment, the activity of Mkk3b is increased. As will be appreciated by those in the art, this may be accomplished in any number of ways. In a preferred embodiment, the activity of Mkk3b is increased by increasing the amount of Mkk3b in the cell, for example by overexpressing the endogenous Mkk3b or by administering a gene encoding a Mkk3b protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety.

In one embodiment, the activity of Mkk3b is decreased. As will be appreciated by those in the art, this may be accomplished in any number of ways. In a preferred embodiment, the activity of Mkk3b is decreased by decreasing the amount of Mkk3b mRNA in the cell, for example by expressing Mkk3b antisense RNA. Alternatively, endogenous Mkk3b activity is decreased by administering anti-Mkk3b antibody or a gene encoding anti-Mkk3b antibody or an epitope recognizing portion thereof. Known gene-therapy techniques may be used to administer these agents. In a preferred embodiment, the gene therapy techniques involve incorporation of the exogenous gene into the host genome using enhanced homologous recombination (EHR), for example as described in PCT/US93/03868, hereby incorporated by reference in its entirety.

Without being bound by theory, it appears that Mkk3b protein is an important protein in lymphocyte activation. Accordingly, disorders of lymphocyte activation mediated by mutant or variant Mkk3b genes or dysregulated Mkk3b gene expression may be determined. In one embodiment, the invention provides methods for identifying cells containing variant Mkk3b genes comprising determining all or part of the sequence of at least one endogenous Mkk3b gene in a cell. As will be appreciated by those in the art, this may be done using any number of sequencing techniques. In a preferred embodiment, the invention provides methods of identifying the Mkk3b genotype of an individual comprising determining all or part of the sequence of at least one Mkk3b gene of the individual. This is generally done in at least one tissue of the individual, and may include the evaluation of a number of tissues or different samples of the same tissue. The method may include comparing the sequence of the sequenced Mkk3b gene to a known Mkk3b gene, i.e. a wild-type gene.

The sequence of all or part of the Mkk3b gene can then be compared to the sequence of a known Mkk3b gene to determine if any differences exist. This can be done using any number of known sequence identity programs, such as Bestfit, etc. In a preferred embodiment, the presence of a difference in the sequence between the Mkk3b gene of the patient and the known Mkk3b gene is indicative of a disease state or a propensity for a disease state.

In one embodiment, the invention provides methods for diagnosing a Mkk3b related condition in an individual. The methods comprise measuring the activity of Mkk3b in a tissue from the individual or patient, which may include a measurement of the amount or specific activity of a Mkk3b protein. This activity is compared to the activity of Mkk3b from either an unaffected second individual or from an unaffected tissue from the first individual. When these activities are different, the first individual may be at risk for a Mkk3b associated disorder. In this way, for example, monitoring of various disease conditions may be done, by monitoring the absolute Mkk3b activity in a sample or the specific activity of a Mkk3b protein from a sample. Similarly, activity levels may correlate with prognosis.

In one aspect, the expression levels of Mkk3b protein genes are determined in different patient samples or cells for which either diagnosis or prognosis information is desired. Gene expression monitoring is done on genes encoding Mkk3b proteins. In one aspect, the expression levels of Mkk3b protein genes are determined for different cellular states, such as normal cells and cells undergoing apoptosis or transformation. By comparing Mkk3b protein gene expression levels in cells in different states, information including both up- and down-regulation of Mkk3b protein genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising sets of important Mkk3b protein genes, such as those of the present invention, which can then be used in these screens. These methods can also be done on the protein basis; that is, protein expression levels of the Mkk3b proteins can be evaluated for diagnostic purposes or to screen candidate agents. In addition, the Mkk3b protein nucleic acid sequences can be administered for gene therapy purposes, including the administration of antisense nucleic acids, or the Mkk3b proteins administered as therapeutic drugs.

Mkk3b protein sequences bound to biochips include both nucleic acid and amino acid sequences as defined above. In a preferred embodiment, nucleic acid probes to Mkk3b protein nucleic acids (both the nucleic acid sequences having the sequences outlined in the Figures and/or the complements thereof) are made. The nucleic acid probes attached to the biochip are designed to be substantially complementary to the Mkk3b protein nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions. In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155-200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix Gene-Chip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology 14:1675-1680 (1996), hereby expressly incorporated by reference. Other techniques include, but are not limited to, quantitative reverse transcriptase PCR, Northern analysis and RNase protection.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the Mkk3b protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an Mkk3b protein is detected by binding the digoxygenin with an anti-digoxygenin secondary antibody and developed with nitro blue tetrazolium and 5-bromo-4-chloro-3-indoyl phosphate.

In another preferred method, expression of Mkk3b protein is determined using in situ imaging techniques employing antibodies to Mkk3b proteins. In this method cells are contacted with from one to many antibodies to the Mkk3b protein(s). Following washing to remove non-specific antibody binding, the presence of the antibody or antibodies is detected. In one embodiment the antibody is detected by incubating with a secondary antibody that contains a detectable label. In another method the primary antibody to the Mkk3b protein(s) contains a detectable label. In another preferred embodiment each one of multiple primary antibodies contains a distinct and detectable label. This method finds particular use in simultaneous screening for a plurality of Mkk3b proteins. The label may be detected in a fluorometer which has the ability to detect and distinguish emissions of different wavelengths. In addition, a fluorescence activated cell sorter (FACS) can be used in this method. As will be appreciated by one of ordinary skill in the art, numerous other histological imaging techniques are useful in the invention and the antibodies can be used in ELISA, immunoblotting (Western blotting), immunoprecipitation, BIA-CORE technology, and the like.

In one embodiment, the Mkk3b proteins of the present invention may be used to generate polyclonal and monoclonal antibodies to Mkk3b proteins, which are useful as described herein. Similarly, the Mkk3b proteins can be coupled, using standard technology, to affinity chromatography columns. These columns may then be used to purify Mkk3b antibodies. In a preferred embodiment, the antibodies are generated to epitopes unique to the Mkk3b protein; that is, the antibodies show little or no cross-reactivity to other proteins. These antibodies find use in a number of applications. For example, the Mkk3b antibodies may be coupled to standard affinity chromatography columns and used to purify Mkk3b proteins as further described below. The antibodies may also be used as blocking polypeptides, as outlined above, since they will specifically bind to the Mkk3b protein.

The anti-Mkk3b protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Mkk3b protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-Mkk3b protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the Mkk3b protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against Mkk3b protein. Preferably, the binding specificity of monoclonal antibodies produced by the hybridoma cells is determined by immunoprecipitation or by an in vitro binding assay, such as radioimmunoassay (RIA) or enzymelinked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

The anti-Mkk3b protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*

321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.,* 227:381 (1991); Marks et al., *J. Mol. Biol.* 222:581 (1991)]. The techniques of Cole et al. and Boemer et al. are also available for the preparation of human monoclonal antibodies (Cole et al., *Monoclonal Antibodies and Cancer Therapy,* Alan R. Liss, p.77 (1985) and Boemer et al., *J. Immunol.,* 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology* 10, 779-783 (1992); Lonberg et al., *Nature* 368 856-859 (1994); Morrison, *Nature* 368, 812-13 (1994); Fishwild et al., *Nature Biotechnology* 14, 845-51 (1996); Neuberger, *Nature Biotechnology* 14, 826 (1996); Lonberg and Huszar, *Intern. Rev. Immunol.* 13 65-93 (1995).

Bispecific antibodies are monoclonal, preferably human or humanized, antibodies that have binding specificities for at least two different antigens. In the present case, one of the binding specificities is for the Mkk3b protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature,* 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-Mkk3b protein antibodies of the invention have various utilities. For example, anti-Mkk3b protein antibodies may be used in diagnostic assays for an Mkk3b protein, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: a Manual of Techniques,* CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, 35S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-Mkk3b protein antibodies also are useful for the affinity purification of Mkk3b protein from recombinant cell culture or natural sources. In this process, the antibodies against Mkk3b protein are immobilized on a suitable support, such a Sephadex resin or filter paper, using methods well known in the art. The immobilized antibody then is contacted with a sample containing the Mkk3b protein to be purified, and thereafter the support is washed with a suitable solvent that will remove substantially all the material in the sample except the Mkk3b protein, which is bound to the immobilized antibody. Finally, the support is washed with another suitable solvent that will release the Mkk3b protein from the antibody.

The anti-Mkk3b protein antibodies may also be used in treatment. In one embodiment, the genes encoding the antibodies are provided, such that the antibodies bind to and modulate the Mkk3b protein within the cell.

In one aspect, the present invention provides antibodies that specifically bind to Mkk3b but not to Mkk3. In a preferred embodiment, such antibodies bind to a determinant set forth by the first 29 amino acids of SEQ ID NO:2.

In one embodiment, a therapeutically effective dose of an Mkk3b protein, agonist or antagonist is administered to a patient. By therapeutically effective dose herein is meant a dose that produces the effects for which it is administered. The exact dose will depend on the purpose of the treatment, and will be ascertainable by one skilled in the art using known techniques. As is known in the art, adjustments for Mkk3b protein degradation, systemic versus localized delivery, as well as the age, body weight, general health, sex, diet, time of administration, drug interaction and the severity of the condition may be necessary, and will be ascertainable with routine experimentation by those skilled in the art.

A patient for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the Mkk3b protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1-100% wt.

The pharmaceutical compositions of the present invention comprise an Mkk3b protein, agonist or antagonist (including antibodies and bioactive agents as described herein, most preferably small molecule chemical compositions as described herein) in a form suitable for administration to a patient. In the preferred embodiment, the pharmaceutical compositions are in a water soluble form, such as being present as pharmaceutically acceptable salts, which is meant to include both acid and base addition salts. Pharmaceutically acceptable acid addition salt refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of Mkk3b protein related disorders with an antibody raised against a Mkk3b protein. As used herein, immunotherapy can be passive or active. Passive immunotherapy, as defined herein, is the passive transfer of antibody to a recipient (patient). Active immunization is the induction of antibody and/or T cell responses in a recipient (patient). Induction of an immune response can be the consequence of providing the recipient with an Mkk3b protein antigen to which antibodies are raised. As appreciated by one of ordinary skill in the art, the Mkk3b protein antigen may be provided by injecting an Mkk3b protein against which antibodies are desired to be raised into a recipient, or contacting the recipient with an Mkk3b protein nucleic acid, capable of expressing the Mkk3b protein antigen, under conditions for expression of the Mkk3b protein antigen.

In a preferred embodiment, a therapeutic compound is conjugated to an antibody, preferably an Mkk3b protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis, cancer Mkk3b protein related disorders. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against Mkk3b proteins, or binding of a radionuclide to a chelating agent that has been covalently attached to the antibody.

In a preferred embodiment, Mkk3b protein genes are administered as DNA vaccines, either single nucleic acids or combinations of Mkk3b protein genes. Naked DNA vaccines are generally known in the art; see Brower, Nature Biotechnology 16:1304-1305 (1998). Methods for the use of nucleic acids as DNA vaccines are well known to one of ordinary skill in the art, and include placing an Mkk3b protein gene or portion of an Mkk3b protein nucleic acid under the control of a promoter for expression in a patient. The Mkk3b protein gene used for DNA vaccines can encode full-length Mkk3b proteins, but more preferably encodes portions of the Mkk3b proteins including peptides derived from the Mkk3b protein. In a preferred embodiment a patient is immunized with a DNA vaccine comprising a plurality of nucleotide sequences derived from a Mkk3b protein gene. Similarly, it is possible to immunize a patient with a plurality of Mkk3b protein genes or portions thereof, as defined herein. Without being bound by theory, following expression of the polypeptide encoded by the DNA vaccine, cytotoxic T cells, helper T cells and antibodies are induced which recognize and destroy or eliminate cells expressing Mkk3b proteins.

In a preferred embodiment, the DNA vaccines include a gene encoding an adjuvant molecule with the DNA vaccine. Such adjuvant molecules include cytokines that increase the immunogenic response to the Mkk3b protein encoded by the DNA vaccine. Additional or alternative adjuvants are known to those of ordinary skill in the art and find use in the invention.

The examples described herein serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited are expressly incorporated herein by reference in their entirety. Moreover, all sequences displayed, cited by reference or accession number in the references are incorporated herein by reference.

EXAMPLES

Example 1

Western blot analysis demonstrated that Mkk3b WT, Mkk3b inactive mutant (AA), Mkk3b inactive mutant (K93A), and activated Mkk3b (EE) fusion proteins could all be expressed in BJAB cells (data not shown).

Example 2

Retroviral expression vectors were used to express epitope-tagged Mkk3b in B cells. The overexpression of Mkk3b in these lymphocytes led to the potentiation of CD69 induction and NFAT activity in response to BCR stimulation and CD40 activation. In the presence of a specific inhibitor of p38 MAPK, MKK3b overexpression did not potentiate the upregulation of CD69 expression nor the induction of NFAT activity in response to these stimuli (see FIGS. 3 and 4).

Example 3

MKK3b Enhances NFAT Activity and CD69 Upregulation

Figure 3:
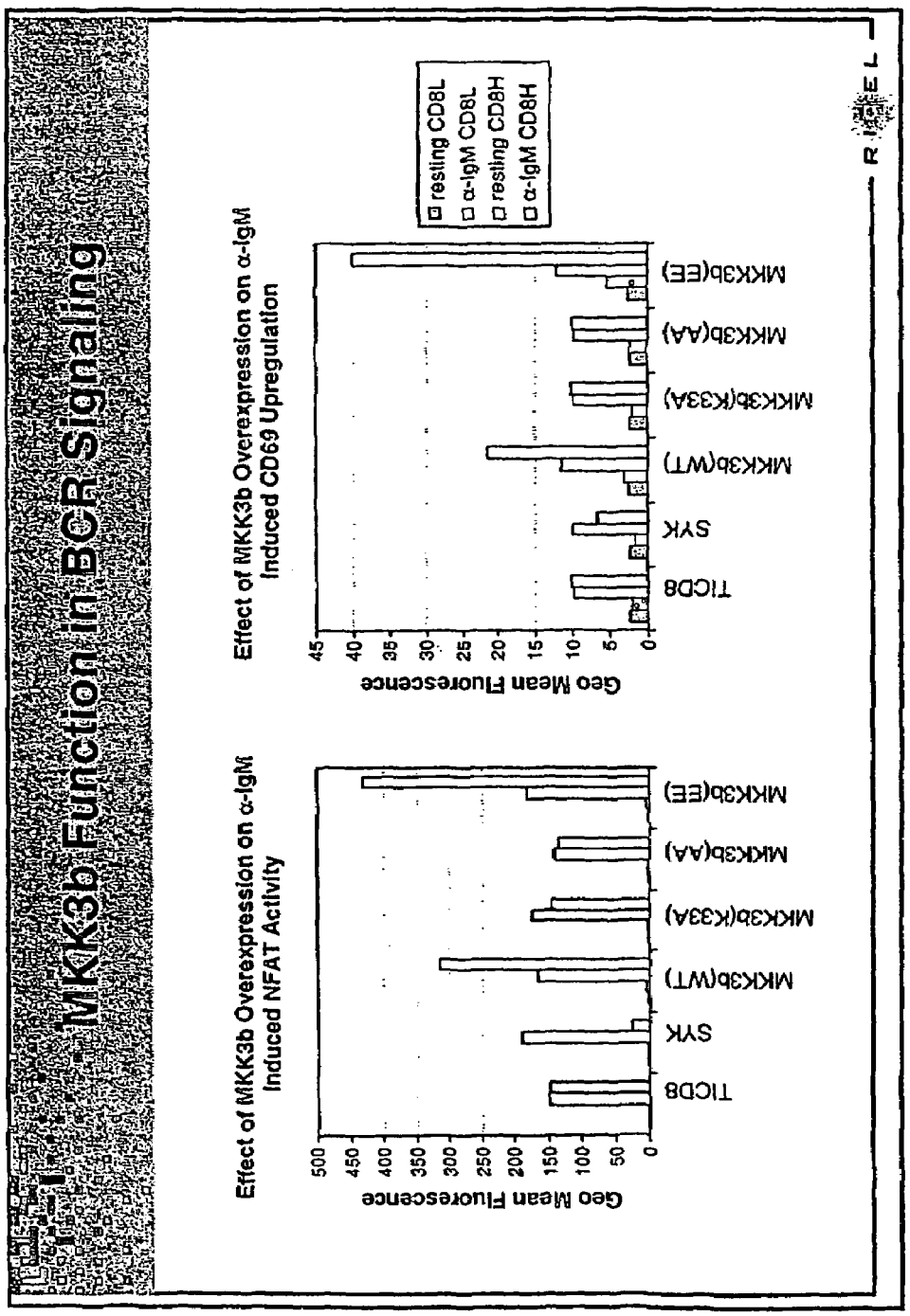
FIG. 3 shows the effect of Mkk3b and variant Mkk3b overexpression on BCR induced NFAT activity (left graph) and the effect of Mkk3b and variant Mkk3b overexpression on BCR induced CD69 upregulation (right graph). Wildtype Mkk3b and constitutively active Mkk3b enhance the induction of NFAT activity and CD69 expression by BCR stimulation.
Figure 4:
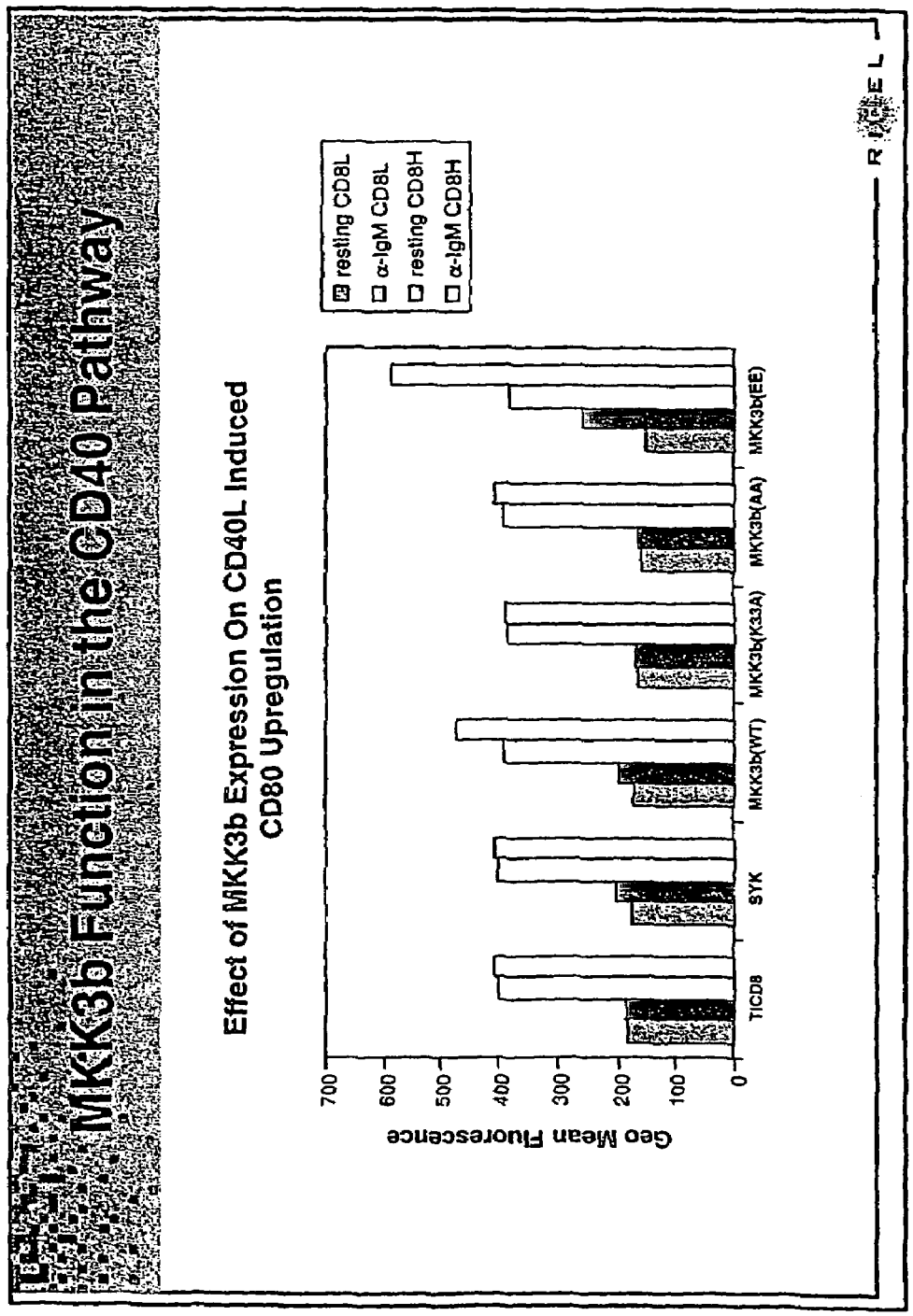
FIG. 4 shows the effect of Mkk3b and variant Mkk3b overexpression on the effect of CD40 induced CD80 expression. CD40 is activated using CD40L. Wildtype Mkk3b and constitutively active Mkk3b enhance the induction of CD80 by CD40.

BJAB-tTA cells (Clone 28) stably infected with the NFAT-GFP reporter construct were infected with TICD8, or TICD8 containing MKK3b (EE), MKK3b (WT), or MKK3b (AA). The infected cells were then stimulated with or without anti-IgM for 24 hours and NFAT activity was assessed by CD8 staining and FACs analysis. The results were computed as the ratio of geometric mean fluorescence of GFP in CD8– and CD8+ cells. Anti-IgM stimulation caused an ~100 fold increase in GFP expression indicating that the NFAT-GFP reporter cells are extremely sensitive to BCR cross-linking. Overexpression of constitutively active MKK3b (EE) or wild-type MKK3b enhanced both basal and anti-IgM-induced NFAT activity. As expected, MKK3b (EE) had a more potent effect than the wild-type construct. In contrast, MKK3b (AA) did not significantly increase the basal or induced levels of NFAT activity. (FIG. 3)

To test the effect of MKK3b overexpression on CD69 regulation, BJAB-tTA cells were infected with various MKK3b constructs and CD69 expression was assayed in CD8– and CD8+ populations. Both MKK3b (EE) and MKK3b (WT) enhanced basal and anti-IgM-induced levels of CD69. Therefore, MKK3b overexpression is sufficient for NFAT activation and CD69 upregulation.

Example 4

Mkk3b bound Btk in a yeast two hybrid assay in which Btk was used as bait. (data not shown)

Example 5

MKK3b did not Enhance BCR Induced IgH Promoter

To test whether MKK3b globally affects gene regulation we assessed the affect of MKK3b overexpression on the IgH promoter in BJABs. BJAB-tTA cells stably transduced with the IgH promoter-GFP reporter cassette were infected with retroviral vectors (TICD8) containing Syk dominant negative (Syk (DN)), MKK3b (EE), or MKK3b (WT). 48 hrs later, the infected cells were stimulated with anti-IgM and GFP expression was determined in CD8– and CD8+ cells by FACs. Comparing the geometric means of GFP fluorescence in CD8– and CD8+ infected cells revealed that neither MKK3b (EE) nor MKK3b (WT) significantly induced the IgH promoter. These results suggest that MKK3 acts in selected pathways to regulate BCR signaling and does not globally control B cell activation. (data not show)

Example 6

Overexpression of wildtype Mkk3b in tTABJAB cells and kinase dead mutant of Mkk3b did not enhance CD69 expression induced by TCR activation in Jurkat T cells. (data not shown)

Example 7

MKK3b Synergizes with a Calcium Signal to Activate NFAT in Jurkat TAg Cells

Figure 7:
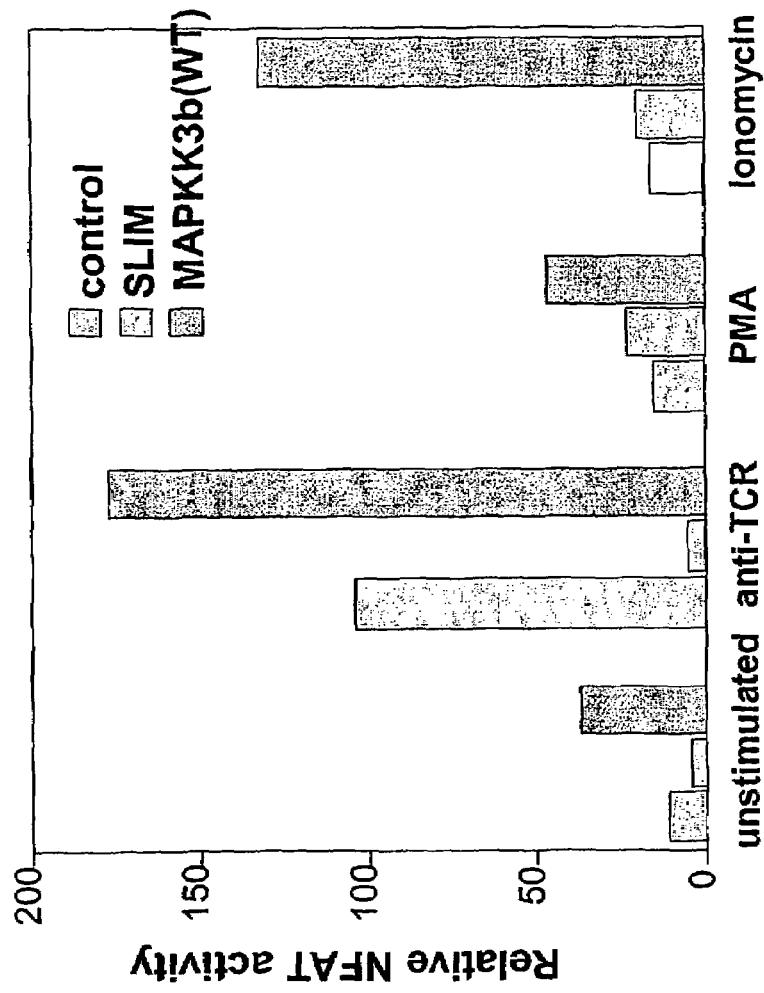
FIG. 7 shows the results of overexpressing SLIM, Mkk3b or kinase dead Mkk3b in Jukat-NFAT-GFP cells. Mkk3b enhances TCR-induced NFAT activity and synergizes with ionomycin to induce NFAT activity. Kinase dead Mkk3b does not enhance TCR-induced NFAT activity or synergize with ionomycin.

NFAT activation requires both calcium mobilization and the PKC pathway, which is activated by phorbol esters (Hivroz-Burgaud, et al. 1991; Baier-Bitterlich, et al. 1996). To further define the mechanism by which MKK3 regulates NFAT we tested whether MKK3b overexpression could replace either phorbol ester or calcium-mediated signaling. Jurkat TAg cells were electroporated with transient transfection vectors encoding MKK3b (WT; 40 mg) or SLIM (40 mg) in addition to the NFAT-luciferase reporter plasmid (10 mg) and the control TK-luciferase plasmid (2 mg). 48 hours later the cells were stimulated with media, anti-TCR antibodies (300 ng/mL; C305), PMA (50 ng/mL), or ionomycin (1 mM) for 16-20 hours. The cell lysates were analyzed for luciferase activity by plate-based luminometry. MKK3b overexpression enhanced both basal and anti-TCR-stimulated NFAT activity. In addition, MKK3b overexpressing cells treated with ionomycin activated NFAT to the same degree as control cells stimulated with anti-TCR. However, MKK3b overexpression did not synergize with PMA to activate NFAT. Therefore, MKK3b can replace the phorbol ester signals and act in conjunction with calcium mobilization to induce NFAT transcriptional activity. (FIG. 7)

Example 8

Northern analysis of Mkk3b mRNA expression showed that Mkk3b is expressed in tissues of the immune system, including the spleen and thymus. Further, PCR-based analysis of Mkk3b expression showed that Mkk3b is highly expressed in bone marrow cells, peripheral blood lymphocytes, and a variety of purified human lymphocytes including resting and activated CD19+ cells, resting and activated CD8+ cells, resting and activated peripheral blood monocytes, resting and activated CD4+ cells, and resting and activated CD8+ cells. (data not shown)

Example 9

Signaling Defects in Mkk3 Deficient Mice

B cell purification and stimulation protocols were optimized using 8-10 week old C57BL/6 mice. Frozen splenocytes (90% FCS, 10% DMSO) were incubated in flasks (2 hrs, 37° C.) to remove monocytes, and then passed through a CD43 negative selection column (Milltenyi, MACS). FACS analysis with anti-CD 19-FITC conjugated antibodies consistently revealed >95% pure B cell populations. The purified B cells were then stimulated in 96 well plates (100,000 cells/well) for 24, 48, or 72 hrs with various concentrations of anti-IgM antibodies, CD40 antibodies, a baculoviral supernatant containing the hCD8-CD40L fusion protein, or Salmonella LPS. The cells were then stained with anti-CD19-FITC in combination with PE-conjugated antibodies recognizing CD80, CD86, CD69, CD25, or CD54 and two-color FACs was performed. Most markers showed maximal expression at 48 hrs and this time point was used for further studies of MKK3−/−mice splenocytes.

Figure 10:
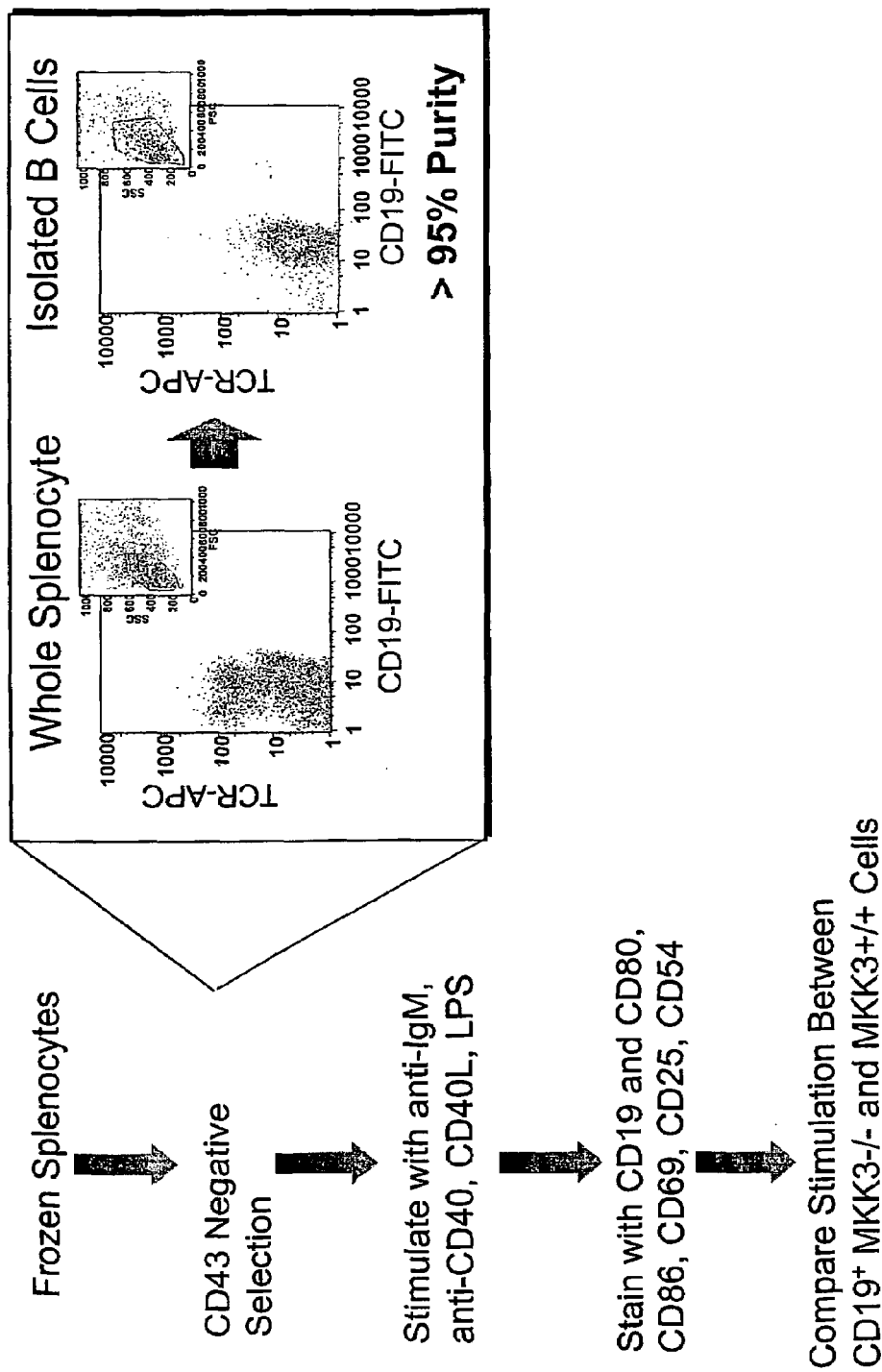
FIG. 10 illustrates the B cell purification and stimulation protocol used in comparing Mkk3−/− and Mkk3+/+murine B cells.

Five frozen spleens from MKK3-deficient mice (Lu et al., EMBO J. 18:1845-1857, 1999) on a C57BL/6 background with appropriate age and sex-matched controls (C57BL6, 9 week old females) were purchased from Richard Flavell's laboratory (Yale University). The spleens were prepared in freezing media (90% FCS, 10% DMSO), and frozen before delivery. Two spleens were required to provide enough cells for one experiment to examine all surface markers (CD80, CD86, CD69, CD25, CD54) under all stimulation conditions (anti-IgM, anti-CD40, hCD8-CD40L, LPS). (See FIGS. 10 and 11).

Figure 12:
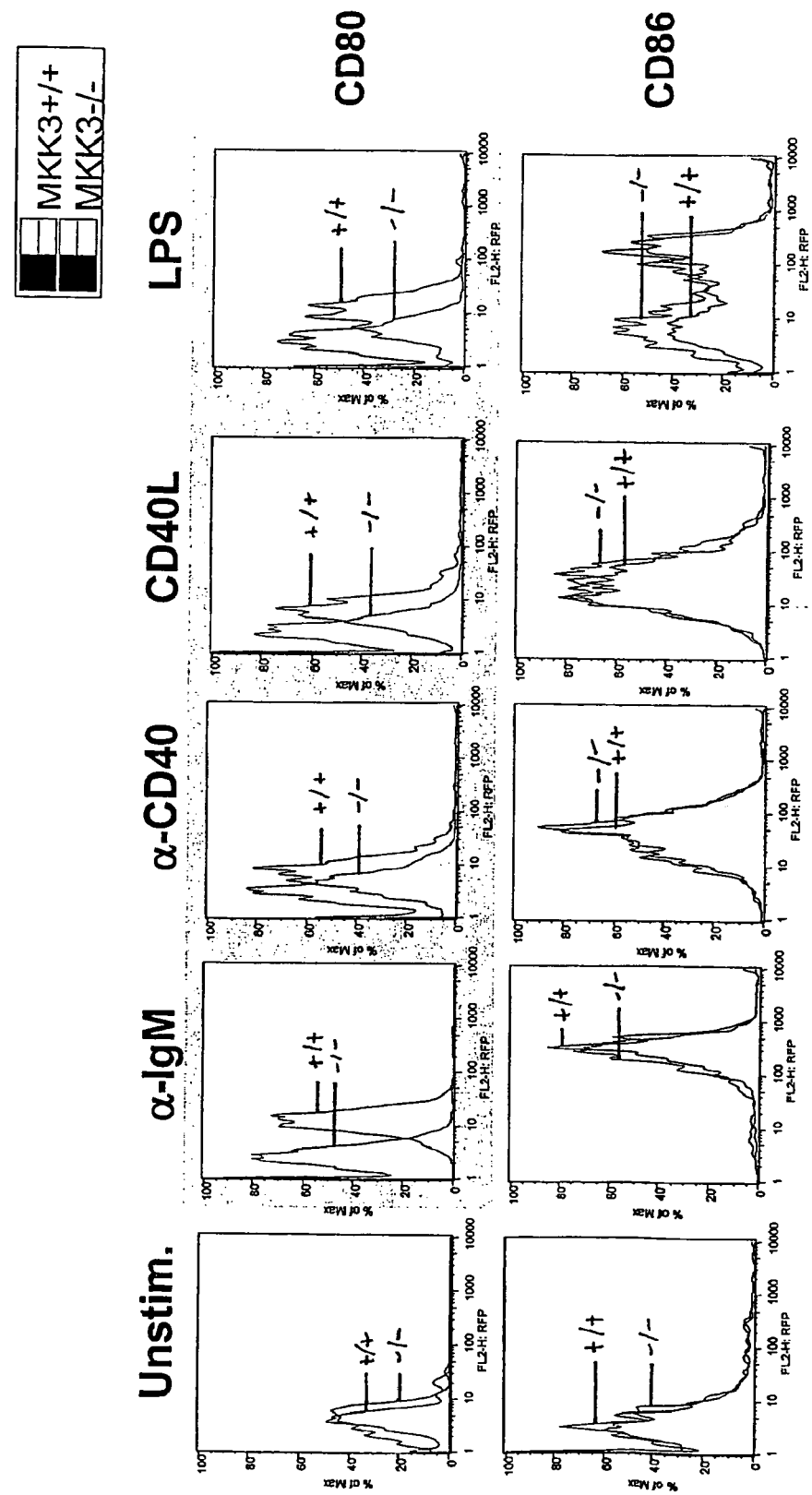
FIG. 12 depicts FACS analyses showing that Mkk3 deficient B cells exhibit defects in CD80 upregulation, but not CD86 upregulation. CD80 induction is triggered in these experiments with a variety of agents, as indicated. Unstimulated cells were used as a control.
Figure 13:
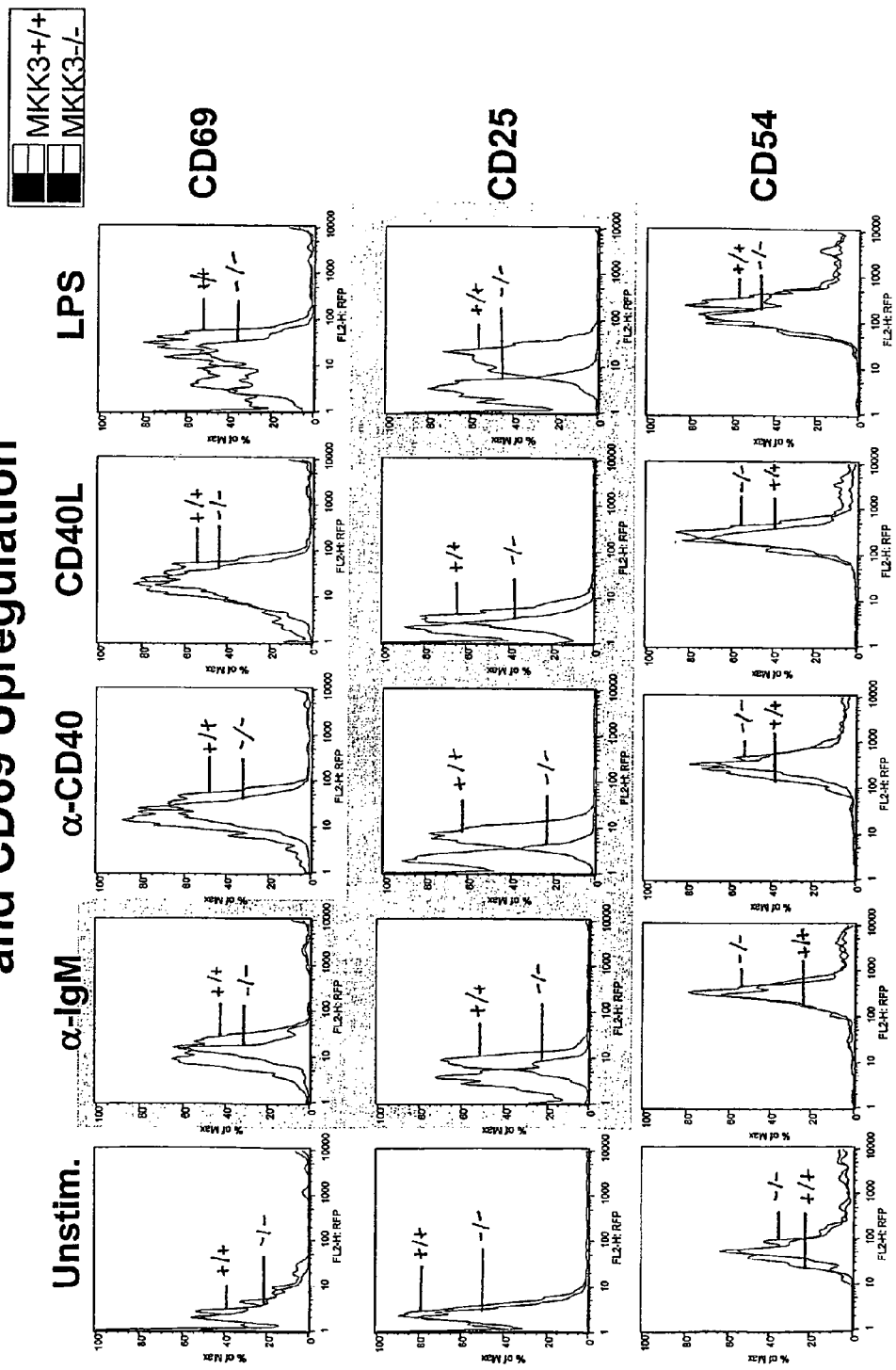
FIG. 13 depicts FACS analyses showing Mkk3 deficient B cells exhibit Defects in CD25 and CD69 upregulation, but not CD54 upregulation, in response to a variety of stimuli.

MKK3-Deficient B Cells Exhibit Specific Defects in CD25, CD69, and CD80 Upregulation B cells were purified from MKK3−/− and wild-type spleens as described above and stimulated using optimal concentrations of anti-IgM, anti-CD40, hCD8-CD40L, and LPS. (see FIG. 11) 48 hrs later the cells were stained with anti-CD19-FITC plus PE-labeled antibodies against CD80, CD86, CD69, CD25, and CD54 and analyzed by FACs. The results are presented as an overlay of MKK3−/− versus wild-type B cells. Relative to wild-type cells, B cells from MKK3−/− mice failed to upregulate CD80 and CD25 in response to all stimuli tested. CD69 upregulation was also defective in response to anti-IgM stimulation and to a lesser extent in response to CD40 agonists and LPS. MKK3 appears to act selectively in BCR and CD40 signaling pathways since CD86 and CD54 induction was not affected. Therefore, MKK3 is selectively involved in the upregulation of several cell surface molecules critical for B cell function and the inflammatory response. (FIGS. 12 and 13)

Example 10

Constructs Used for Functional Studies of MKK3b

Figure 8:
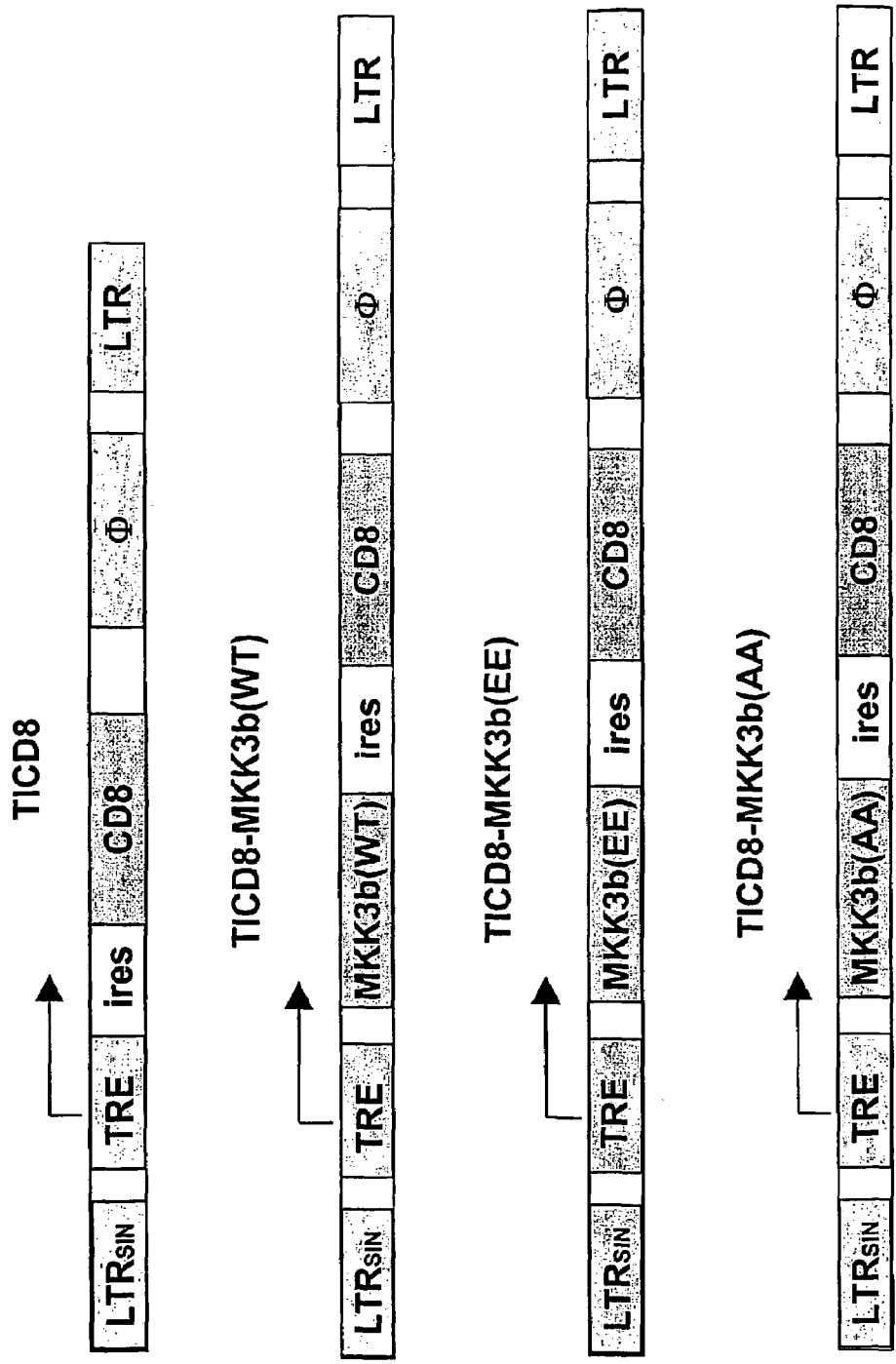
FIG. 8 is a schematic showing Mkk3b the constructs used in the functional studies.
Figure 9:
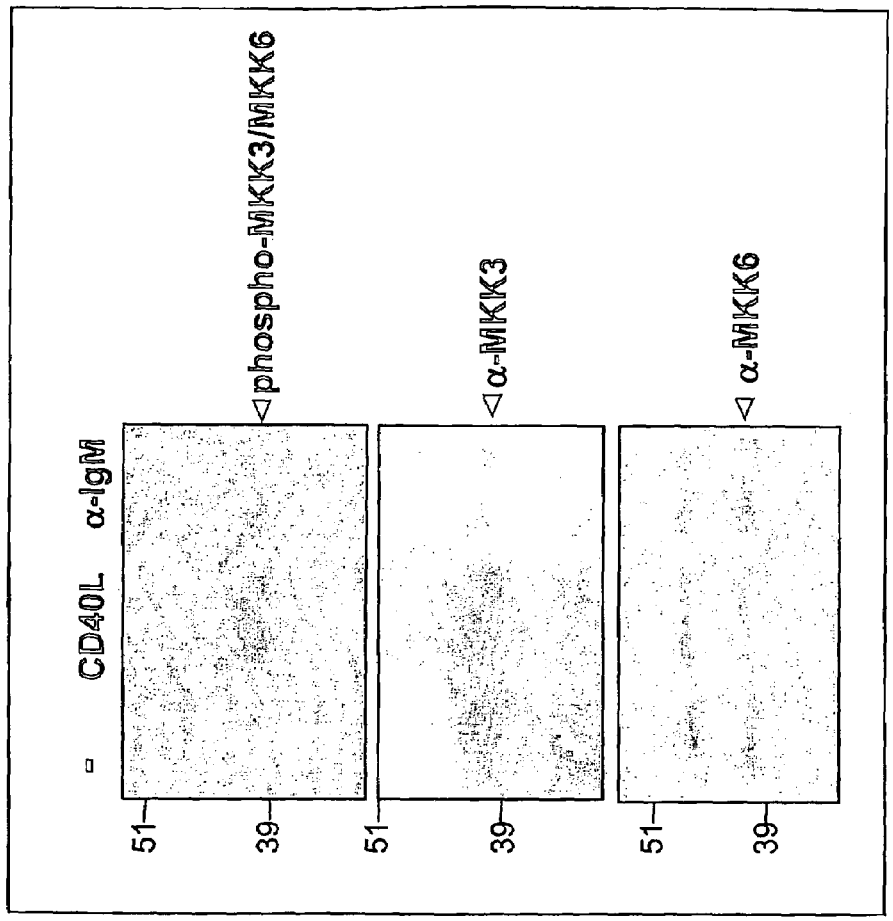
FIG. 9 shows three Western blots that demonstrate CD40L and anti-IgM activate endogenous Mkk3/Mkk6 in purified primary B cells. Human B cells were negatively selected using antibodies against CD2, CD3, CD7, CD14, CD16 and CD56 to obtain a human B cell population of greater than 90% purity from peripheral blood mononuclear cells.

TRA-IRES-CD8 vectors (TICD8) contain a tetracycline responsive element (TRE)-IRES-CD8 cassette flanked by a 3′ retroviral packaging sequence (Φ), and LTR, and a 5′ self-inactivating LTR. TICD8-MKK3b (WT), MKK3b (EE), and MKK3b (AA), contain open reading frames controlled by the TRE. We used MKK3b instead of MKK3 because this isoform more efficiently phosphorylates and activates p38. MKK3b (EE) is the constitutively active mutant whereas MKK3b (AA) is the inactive version. (see FIG. 8)

Example 11

MKK3b Potentiates CD40L-Induced p38 Activation

BJAB-tTA cells (clone 28) were infected with retroviruses containing either TICD8 or TICD8-MKK3b(WT). 48 hours later the cells were FACs sorted for CD8high cells then stimulated with rCD40L (10 mg/mL) or anti-IgM (0.5 mg/mL). The cells were lysed, then analyzed by western blot using anti-phospho-p38 antibodies as a probe. In TICD8-infected cells, CD40L induced moderate levels of p38 phosphorylation while anti-IgM failed to induce significant p38 activation. However, in MKK3b (WT)-infected cells, the basal level of phosphorylated p38 protein dramatically increased compared with the basal level in cells infected with vector (TICD8). In addition, MKK3b overexpression potentiated CD40L-induced p38 phosphorylation. In contrast, MKK3b did not appear to potentiate p38 activation triggered by BCR cross-linking. (data not shown)

We claim:

1. A method of screening for a bioactive agent capable of modulating lymphocyte activation, said method comprising:

i) providing a lymphocyte comprising a recombinant nucleic acid molecule encoding a recombinant protein which is expressed in said lymphocyte to produce the protein, wherein said protein comprises a Mkk3b polypeptide having at least 95% identity to SEQ ID NO: 2 and having kinase activity;

ii) contacting said lymphocyte with a candidate bioactive agent;

ii) inducing activation of said lymphocyte; and iv) determining the activation of said lymphocyte in the presence of said candidate bioactive agent, wherein said activation is determined by measuring the surface expression of CD69, CD80, or CD25, or by measuring p38 phosphorylation, or by measuring NFAT activity;

wherein a change in the activation of said lymphocyte in the presence of said candidate bioactive agent indicates that said candidate bioactive agent is capable of modulating lymphocyte activation.

2. The method according to claim 1, wherein said lymphocyte is a B-lymphocyte.

3. The method according to claim 2, wherein said B-lymphocyte comprises a BCR, and wherein inducing activation of said lymphocyte is done by stimulating said BCR.

4. The method according to claim 2, wherein said B-lymphocyte comprises a CD40 protein complex, and wherein inducing activation of said lymphocyte is done by stimulating said CD40 protein complex.

5. The method according to claim 2, wherein one or more candidate bioactive agents are contacted to the B-lymphocyte.

6. The method according to claim 1, wherein said lymphocyte is a T-lymphocyte.

7. The method according to claim 6, wherein said T-lymphocyte comprises a TCR, and wherein inducing activation of said lymphocyte is done by stimulating said TCR.

8. The method according to claim 6, wherein one or more candidate bioactive agents are contacted to the T-lymphocyte.

9. The method according to claim 6, wherein determining the activation of said T-lymphocyte involves measuring NFAT activity.

10. The method according to claim 1, further comprising:
  v) providing a sample comprising recombinant Mkk3b protein, wherein said recombinant Mkk3b protein comprises an amino acid sequence having at least 95% identity to SEQ ID NO:2 and has kinase activity;
  vi) contacting said sample with the candidate bioactive agent; and
  vii) detecting a change in the kinase activity of said recombinant Mkk3b protein.

* * * * *

SEQUENCE LISTING

```
<160> NUMBER OF SEQ ID NOS: 2

<210> SEQ ID NO 1
<211> LENGTH: 2103
<212> TYPE: DNA
<213> ORGANISM: Homo sapiens
<220> FEATURE:
<223> OTHER INFORMATION: human MAP kinase kinase 3b (Mkk3b) cDNA
<220> FEATURE:
<221> NAME/KEY: CDS
<222> LOCATION: (58)..(1101)
<223> OTHER INFORMATION: Mkk3b

<400> SEQUENCE: 1
ctcgagatcc attgtgctct aaagagtctc caccgccgtc caggaccac ttgcagcatg      60 gagtcgcccg cctcgagcca gcccgccagc atgcccagt ccaaaggaaa atccaagagg     120
aagaaggatc tacggatatc ctgcatgtcc aagccacccg cacccaaccc cacaccccc     180
```

-continued

```
cggaacctgg actcccggac cttcatcacc attggagaca gaaactttga ggtggaggct    240
gatgacttgg tgaccatctc agaactgggc cgtggagcct atggggtggt agagaaggtg    300
cggcacgccc agagcggcac catcatggcc gtgaagcgga tccgggccac cgtgaactca    360
caggagcaga agcggctgct catggacctg acatcaaca tgcgcacggt cgactgtttc     420
tacactgtca ccttctacgg ggcactattc agagagggag acgtgtggat ctgcatggag    480
ctcatggaca catccttgga caagttctac cggaaggtgc tggataaaaa catgacaatt    540
ccagaggaca tccttgggga gattgctgtg tctatcgtgc gggccctgga gcatctgcac    600
agcaagctgt cggtgatcca cagagatgtg aagccctcca atgtccttat caacaaggag    660
ggccatgtga agatgtgtga ctttggcatc agtggctact tggtggactc tgtggccaag    720
acgatggatg ccggctgcaa gccctacatg gcccctgaga ggatcaaccc agagctgaac    780
cagaagggct acaatgtcaa gtccgacgtc tggagcctgg gcatcaccat gattgagatg    840
gccatcctgc ggttcccttta cgagtcctgg ggaccccgt tccagcagct gaagcaggtg    900
gtggaggagc cgtcccccca gctcccagcc gaccgtttct cccccgagtt tgtggacttc    960
actgctcagt gcctgaggaa gaaccccgca gagcgtatga gctacctgga gctgatggag   1020
caccccttct tcaccttgca caaaaccaag aagacggaca ttgctgcctt cgtgaaggag   1080
atcctgggag aagactcata ggggctgggc ctcggacccc actccggccc tccagagccc   1140
cacagcccca tctgcggggg cagtgctcac ccacaccata agctactgcc atcctggccc   1200
agggcatctg ggaggaaccg aggggctgc tcccacctgg ctctgtggcg agccatttgt    1260
cccaagtgcc aaagaagcag accattgggg ctcccagcca ggcccttgtc ggccccacca   1320
gtgcctctcc ctgctgctcc taggacccgt ctccagctgc tgagatcctg gactgagggg   1380
gcctggatgc cccctgtgga tgctgctgcc cctgcacagc aggctgccag tgcctgggtg   1440
gatgggccac cgccttgccc agcctggatg ccatccaagt tgtatatttt tttaatctct   1500
cgactgaatg gactttgcac actttggccc agggtggcca cacctctatc ccggctttgg   1560
tgcggggtac acaagagggg atgagttgtg tgaataccccc aagactccca tgagggagat   1620
gccatgagcc gcccaaggcc ttcccctggc actggcaaac agggcctctg cggagcacac   1680
tggctcaccc agtcctgccc gccaccgtta tcggtgtcat tcacctttcg tgttttttt    1740 aatttatcct ctgttgattt tttcttttgc tttatgggtt tggcttgttt ttcttgcatg   1800
gtttggagct gatcgcttct cccccacccc ctagggtacc agcaggcaga gccttgccct   1860
ctgctcaggc tggggtccag tgggaggggc ccaaaatctc tgctcagaga agtgcagggg   1920
gagccttcca gctcactctc cctgaggact ggcgtgacag gggctatggg tgttgttttt   1980
aaaaaaagaa aatatatttt tttgaaaaaa cgactgccca tcccgggtcc tttccctgat   2040
gggttggggc agttacctgg ttgctgtttt aattaaaaac tttagagcac aatggatctc   2100
gag                                                                 2103
```

<210> SEQ ID NO 2
<211> LENGTH: 347
<212> TYPE: PRT
<213> ORGANISM: Homo sapiens
<220> FEATURE:
<223> OTHER INFORMATION: human MAP kinase kinase 3b (Mkk3b)

<400> SEQUENCE: 2

```
Met Glu Ser Pro Ala Ser Ser Gln Pro Ala Ser Met Pro Gln Ser Lys
 1               5                  10                  15
```

-continued

```
Gly Lys Ser Lys Arg Lys Lys Asp Leu Arg Ile Ser Cys Met Ser Lys
            20                  25                  30

Pro Pro Ala Pro Asn Pro Thr Pro Pro Arg Asn Leu Asp Ser Arg Thr
        35                  40                  45

Phe Ile Thr Ile Gly Asp Arg Asn Phe Glu Val Glu Ala Asp Asp Leu
    50                  55                  60

Val Thr Ile Ser Glu Leu Gly Arg Gly Ala Tyr Gly Val Val Glu Lys
65                  70                  75                  80

Val Arg His Ala Gln Ser Gly Thr Ile Met Ala Val Lys Arg Ile Arg
                85                  90                  95

Ala Thr Val Asn Ser Gln Glu Gln Lys Arg Leu Leu Met Asp Leu Asp
            100                 105                 110

Ile Asn Met Arg Thr Val Asp Cys Phe Tyr Thr Val Thr Phe Tyr Gly
        115                 120                 125

Ala Leu Phe Arg Glu Gly Asp Val Trp Ile Cys Met Glu Leu Met Asp
    130                 135                 140

Thr Ser Leu Asp Lys Phe Tyr Arg Lys Val Leu Asp Lys Asn Met Thr
145                 150                 155                 160
Ile Pro Glu Asp Ile Leu Gly Glu Ile Ala Val Ser Ile Val Arg Ala
                165                 170                 175
Leu Glu His Leu His Ser Lys Leu Ser Val Ile His Arg Asp Val Lys
            180                 185                 190

Pro Ser Asn Val Leu Ile Asn Lys Glu Gly His Val Lys Met Cys Asp
        195                 200                 205

Phe Gly Ile Ser Gly Tyr Leu Val Asp Ser Val Ala Lys Thr Met Asp
    210                 215                 220

Ala Gly Cys Lys Pro Tyr Met Ala Pro Glu Arg Ile Asn Pro Glu Leu
225                 230                 235                 240
Asn Gln Lys Gly Tyr Asn Val Lys Ser Asp Val Trp Ser Leu Gly Ile
                245                 250                 255
Thr Met Ile Glu Met Ala Ile Leu Arg Phe Pro Tyr Glu Ser Trp Gly
            260                 265                 270

Thr Pro Phe Gln Gln Leu Lys Gln Val Val Glu Glu Pro Ser Pro Gln
        275                 280                 285

Leu Pro Ala Asp Arg Phe Ser Pro Glu Phe Val Asp Phe Thr Ala Gln
    290                 295                 300

Cys Leu Arg Lys Asn Pro Ala Glu Arg Met Ser Tyr Leu Glu Leu Met
305                 310                 315                 320
Glu His Pro Phe Phe Thr Leu His Lys Thr Lys Lys Thr Asp Ile Ala
                325                 330                 335
Ala Phe Val Lys Glu Ile Leu Gly Glu Asp Ser
            340                 345
```